(12) United States Patent
Lederkremer et al.

(10) Patent No.: US 7,741,065 B2
(45) Date of Patent: Jun. 22, 2010

(54) NON-INVASIVE MARKER FOR LIVER FUNCTION AND DISEASE

(75) Inventors: Gerardo Zelmar Lederkremer, Shoham (IL); Maria Kondratyev, Toronto (CA)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 352 days.

(21) Appl. No.: 11/224,148

(22) Filed: Sep. 13, 2005

(65) Prior Publication Data

US 2006/0286615 A1 Dec. 21, 2006

Related U.S. Application Data

(63) Continuation-in-part of application No. PCT/IL2004/000244, filed on Mar. 14, 2004.

(60) Provisional application No. 60/453,944, filed on Mar. 13, 2003, provisional application No. 60/691,241, filed on Jun. 17, 2005.

(51) Int. Cl.
    *G01N 33/574* (2006.01)
(52) U.S. Cl. .................... 435/7.23; 435/7.1
(58) Field of Classification Search .................. None
    See application file for complete search history.

(56) References Cited

U.S. PATENT DOCUMENTS

| | | |
|---|---|---|
| 4,036,945 A | 7/1977 | Haber |
| 4,331,647 A | 5/1982 | Goldenberg |
| 4,816,567 A | 3/1989 | Cabilly et al. |
| 4,946,778 A | 8/1990 | Ladner et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |

FOREIGN PATENT DOCUMENTS

| | | |
|---|---|---|
| EP | 0773289 | 8/1996 |

OTHER PUBLICATIONS

Wisdom Clin. Chem.. vol. 22 p. 1243 (1976).*
Moseley "Evaluation of Abnormal Liver Function Tests", Management of Chronic Liver Disease, 80(5): 887-906, 1996.
Drickamer "Clearing Up Glycoprotein Hormones", Cell, 67: 1029-1032, 1991.
Doyle et al. "Plasma Membrane: Biogenesis and Turnover", The Liver: Biology and Pathobiology, 2nd Ed.(Chap.8): 141-163, 1988.
Gopal et al. "Abnormal Findings on Liver Function Tests: Interpreting Results to Narrow the Diagnosis and Establish A Prognosis", Postgraduate Medicine, 107(2): 100-114, 2000.
Hay et al. "The Nature of Unexplained Chronic Aminotransferase Elevations of A Mild to Moderate Degree in Asymptomatic Patients", Hepatology, 9(2): 193-197, 1989. Abstract.
Hayasaka et al. "Serum Markers as Tools to Monitor Liver Fibrosis", Digestion, 59: 381-384, 1998.
Lederkremer et al. "An Alernatively Spliced Miniexon Alters the Subcellular Fate of the Human Asialglycoprotein Receptor H2 Subunit", The Journal of Biological Chemistry, 266(2): 1237-1244, 1991.
Tolchinsky et al. "Membrane-Bound Versus Secreted Forms of Human Asialglycoprotein Receptor Subunits", The Journal of Biological Chemistry, 271(24): 14496-14503, 1996.
Trojan et al. "Serum Tests for Diagnosis and Follow-Up of Hepatocellular Carcinoma After Treatment", Digestion, 59(Suppl.2): 72-74, 1998.
Yago et al "Detection and Quantification of Soluble Asialglycoprotein Receptor in Human Serum", Hepatplogy, 21:383-388, 1995.
Campbell "General Properties and Applications of Monoclonal Antibodies", Monoclonal Antibody Technology, Elsevier Science Publishers, Chap.1: 1-32, 1984. p. 29.
Hay et al. "The Nature of Unexplained Chronic Aminotransferase Elevations of a Mild to Moderate Degree in Asymptomatic Patients", Hepatology, 9(2): 193-197, 1989.
Supplementary European Search Report Dated Jun. 8, 2009 From the European Patent Office Re.: Application No. 04720548.9.
Bischoff et al. "The H1 and H2 Polypeptides Associate to Form the Asialoglycoprotein Receptor in Human Hepatoma Cells", The Journal of Cell Biology, XP007898593, 106(4): 1067-1974, Apr. 1988. p. 1068, 1-h Col., Last §—r-h Col., § 1.
Henis et al. "Oligomeric Structure of the Human Asialoglycoprotein Receptor: Nature and Stoichiometry of Mutual Complexes Containing H1 and H2 Polypeptides Assessed by Fluorescence Photobleaching Recovery", The Journal of Cell Biology, XP007908595, 111(4): 1409-1418, Oct. 1990. p. 1410, r-h Col., § 2-3.
Kokudo et al. "Predictors of Successful Hepatic Resection: Prognostic Usefulness of Hepatic Asialoglycoprotein Receptor Analysis", Worl Journal of Surgery, XP007908592, 26(11): 1342-1347, Nov. 2002. Abstract.
International Preliminary Report on Patentability Dated Jun. 26, 2008 From the International Bureau of WIPO Re.: Application No. PCT/IL2004/000244.
International Search Report Dated Dec. 18, 2007 From the International Searching Authority Re.: Application No. PCT/IL04/00244.
Invitation to Pay Additional Fees Dated Mar. 14, 2007 From the International Searching Authority Re.: Application No. PCT/IL04/00244.
Written Opinion Dated Dec. 18, 2007 From the International Searching Authority Re.: Application No. PCT/IL04/00244.
Communication Pursuant to Article 94(3) EPC Dated Aug. 21, 2009 From the European Patent Office Re.: Application No. 04720548.9.
Response Dated Dec. 16, 2009 to Communication Pursuant to Article 94(3) EPC of Aug. 21, 2009 From the European Patent Office Re.: Application No. 04720548.9.

* cited by examiner

*Primary Examiner*—Sheela J Huff

(57) ABSTRACT

A monoclonal antibody or fragment thereof, capable of specifically binding to at least one epitope of sH2a and/or being elicited by at least one epitope, and assays, kits, and methods of use thereof diagnosing liver disease or condition, detecting liver function and assessing the efficacy of therapy to a liver disease.

9 Claims, 9 Drawing Sheets

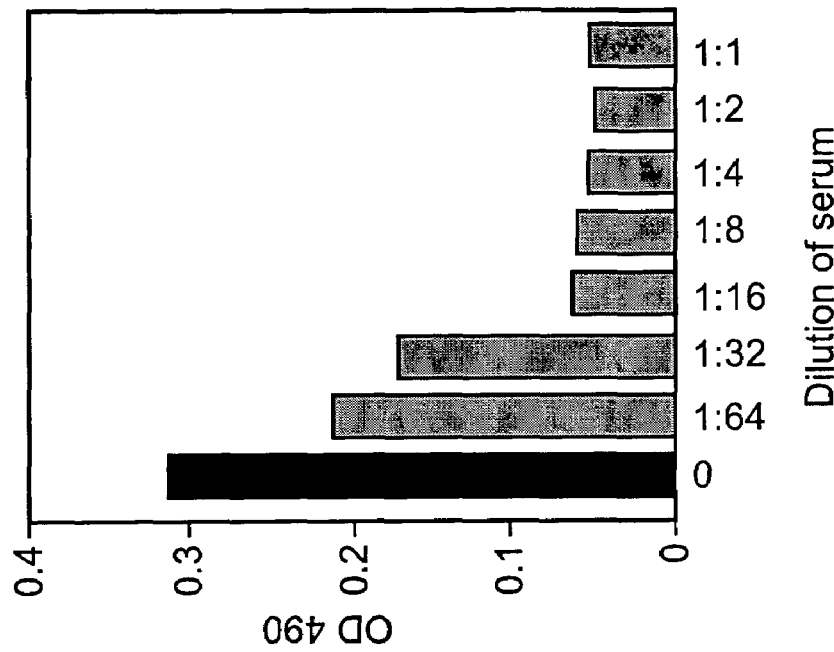
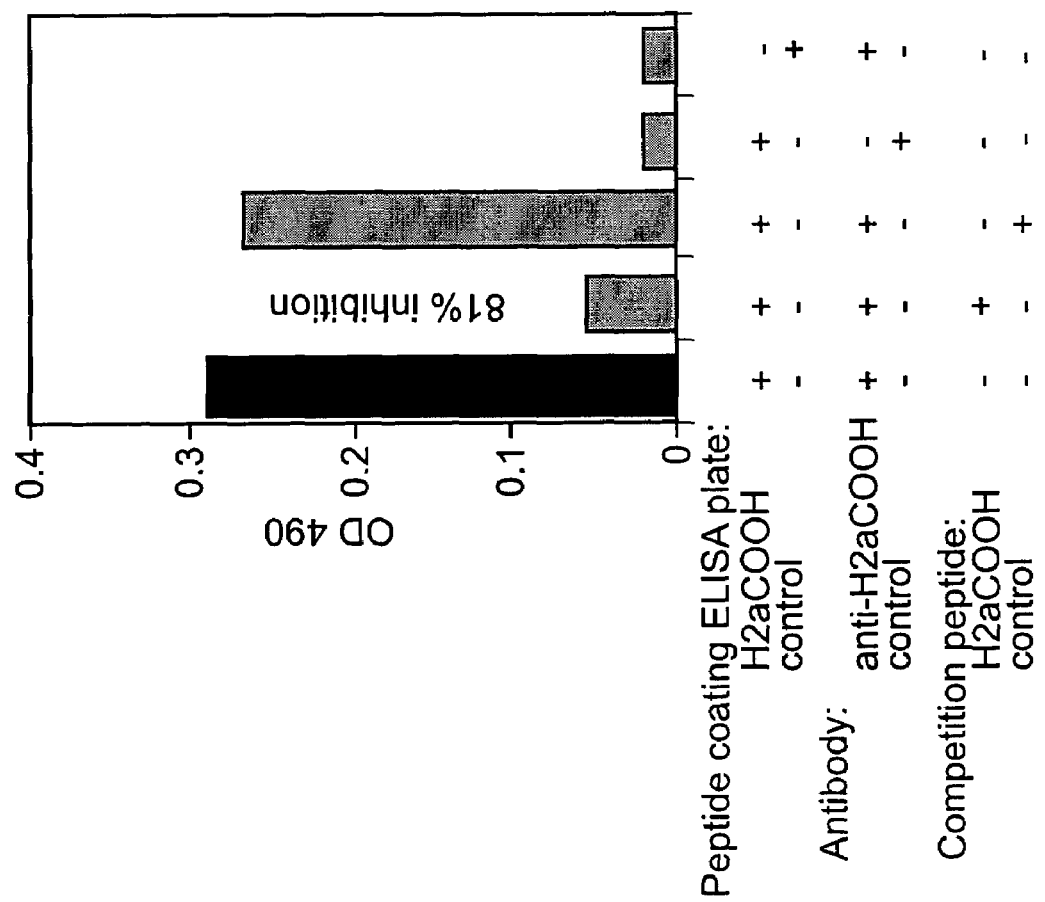
Fig. 4a
Fig. 4b

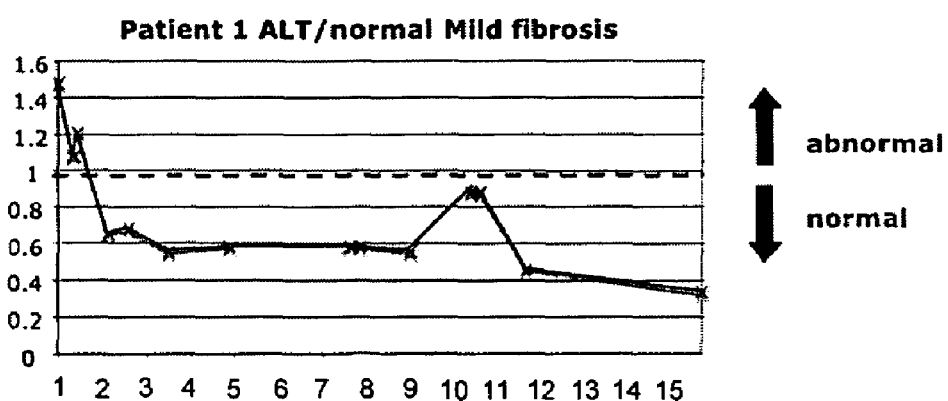
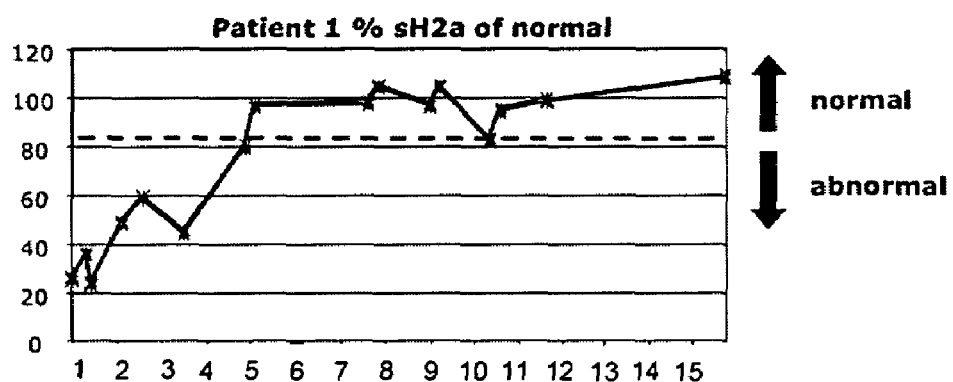

SEQUENCE LISTING

<160> NUMBER OF SEQ ID NOS: 2

<210> SEQ ID NO 1
<211> LENGTH: 12
<212> TYPE: PRT
<213> ORGANISM: Artificial sequence
<220> FEATURE:
<223> OTHER INFORMATION: Synthetic peptide

<400> SEQUENCE: 1

Cys Glu Lys Arg Arg Asn Ala Thr Gly Glu Val Ala
1               5                   10

<210> SEQ ID NO 2
<211> LENGTH: 18
<212> TYPE: PRT
<213> ORGANISM: Artificial sequence
<220> FEATURE:
<223> OTHER INFORMATION: Synthetic peptide

<400> SEQUENCE: 2

Cys Val Thr Gly Ser Gln Ser Glu Gly His Arg Gly Ala Gln Leu Gln
1               5                   10                  15

Ala Glu

NON-INVASIVE MARKER FOR LIVER FUNCTION AND DISEASE

RELATED APPLICATIONS

This application is a Continuation-In-Part (CIP) of PCT Patent Application No. PCT/IL2004/000244, filed on Mar. 14, 2004, which claims priority from U.S. Provisional Application No. 60/453,944, filed on Mar. 13, 2003. This application also claims priority from U.S. Provisional Application No. 60/691,241, filed on Jun. 17, 2005. The contents of the above applications are incorporated herein by reference.

FIELD OF THE INVENTION

The present invention is related to antibodies, kits, assays and methods of use thereof for a soluble non-invasive marker for liver function, liver disease and for diagnosis of success in liver transplantation.

BACKGROUND OF THE INVENTION

Soluble secreted proteins that are expressed uniquely in specific organs, or proteins whose formation or secretion is regulated by disease states, are excellent markers for disease. The reason for this is that the disease can be diagnosed by simply measuring the level of the secreted protein in serum of a potential patient. The level of a secreted protein in serum can be easily measured in a number of different ways that are well known in the art, such as ELISA assay and Western blotting, directed at quantitating marker levels in the serum sample. However, in order to have a good marker for disease, the secreted protein must have distinctly different levels in normal and disease tissues. In order to provide accurate diagnosis in diseases that must be caught at early development stages in order to enable efficient treatment, such as cancer or fibrosis, the marker must have distinct expression or secretion levels even at an early stage of disease development.

Hepatoma, or hepatocellular carcinoma, is the most common primary liver cancer. In certain areas of the world, hepatomas are more common than metastatic liver cancer, and are a prominent cause of death.

Hepatocarcinoma can often arise as a complication of liver cirrhosis. Approximately 2-7% of patients with liver cirrhosis develop hepatocellular carcinoma, and a much higher percentage eventually need a liver transplant due to liver damage caused by the cirrhosis itself.

Liver function can be affected by many chemicals, medicines, diet regimes, environmental poisons, alcohol abuse and viral infections that lead to hepatitis. The most common complications are liver fibrosis and cirrhosis. Generally, the origins of liver fibrosis that leads in its advanced stages to cirrhosis are common complications of Hepatitis B and C.

Hepatitis B is very common in Africa and in Asia, especially in the Philippines and in China and is endemic in the Middle East. In Europe and North America the incidence of known carriers is about 1 in a 1000 people. Worldwide, it is estimated that there are over 350 million hepatitis B (HBV) carriers, which represents 5% of the world's population. In addition it is estimated that 10 to 30 million people are infected with the hepatitis B virus each year. 10% of the people infected with HBV develop chronic infection. People with a chronic HBV infection are at risk of liver damage and around 20-30% of these people later develop cirrhosis (http://hepatitis-central.com/).

Hepatitis C is almost as common, and it is estimated that there are approximately 200 million people worldwide infected with the virus. There are up to 230,000 new HCV infections every year in the U.S. alone. Currently, 8,000 to 10,000 people infected with HCV die each year. Over the next 10-20 years, chronic HCV is predicted to become a major burden on the health care system, as patients who are currently asymptomatic with a relatively mild form of the disease, progress to end-stage liver disease and develop hepatocellular carcinoma. Progressive hepatic fibrosis and cirrhosis develop in 20% to 30% of patients with chronic HCV. There is no vaccine and no completely effective treatment for this virus (http://hepatitis-central.com/). Predictions in the USA indicate that there will be a 60% increase in the incidence of cirrhosis, a 68% increase in hepatoma incidence, a 279% increment in incidence of hepatic decompensation, a 528% increase in the need for transplantation, and a 223% increase in liver death rate. Altogether the number of fibrotic and cirrhotic patients worldwide in need of periodic diagnosis can be estimated at around 20 million, with up to 2 million added each year. With regard to the number of pre-fibrotic patients that would benefit from an early diagnosis, there could be several hundred million worldwide.

Frequently the first symptoms of a hepatoma are abdominal pain, weight loss, and at a later stage of tumor development a large mass that can be felt in the upper right abdomen. However, as the initial symptoms are non-specific, they are often attributed to other possible conditions, and therefore biochemical and histological tests, which would give a more accurate diagnosis, are only performed when the tumor is largely developed.

Generally the survival rate for people in the United States with a hepatoma is poor because the tumor is normally detected at a late stage. In some other countries, such as Japan, the survival rate is higher because of routine screening and thus earlier detection.

Recurrence or development of second liver tumors is very common after therapy of hepatomas. Therefore, screening hepatoma patients with diagnostic methods is extremely important.

The gold standard for diagnosis of hepatomas is liver biopsy, but it cannot be performed on a routine basis, due to the invasiveness involved, and the complexity of the procedure.

Non-invasive serum markers may also be used for diagnosis, however in the case of liver cancer, the existing non-invasive serum markers are not satisfactory for the purpose of diagnosis, and even less suitable for early diagnosis of hepatomas.

The most established non-invasive tumor marker for hepatoma is α-fetoprotein that shows elevated levels following hepatocarcinogenesis. However, about 40% of the patients with small-sized hepatocarcinomas show normal α-fetoprotein levels (1).

As mentioned above, hepatocarcinoma can arise as a complication of liver cirrhosis. In the case of cirrhosis and fibrosis, early diagnosis is necessary to allow any potential treatment. Similar to the case of hepatomas, initial stages of liver fibrosis (e.g. arising from HBV or HCV infections) are asymptomatic or have mild symptoms often attributed to other possible conditions. Therefore, the disease is detected at a stage that is late for an effective treatment.

Generally, blood tests for liver function are based on the level of several markers such as alanine aminotransferase (ALT), aspartate aminotransferase (AST), alkaline phosphatase (ALP), gamma glutamic transpeptidase (GGT), bilirubin, albumin and prothrombin time (PT) in the serum. However, while the markers used in such "liver function tests" are capable of assessing hepatocyte integrity, which might be indicative to liver damage, most of them, except albumin and prothrombin, are not indicative of the synthesis function of the liver. Albumin, which is produced in the liver and circulates in the blood, is affected only when a liver disease is at a severe stage. On the other hand non-hepatic diseases such as nephrotic syndromes can affect albumin levels. Similarly, prothrombin, which is used to evaluate blood clotting disorders, is insensitive to mild liver disease and can be also affected by non-hepatic conditions such as dietary deficiencies or the use of anti-coagulants. Likewise, abnormal levels of bilirubin can result from hemolysis, ineffective erythropoiesis and other non-hepatic syndromes. In addition, as ALT, AST, ALP and GGT are also produced in organs other than the liver, their blood levels can be elevated in a wide range of non-hepatic diseases. Biochemical screening of healthy, asymptomatic people has revealed that up to 6% of the population exhibit abnormal levels of liver enzymes. However, the prevalence of liver disease in the general population is significantly lower (about 1%) (Gopal and Rosen, 2000). Even though the current serum biochemical test pattern may suggest a specific diagnosis, confirmation usually requires further investigation using imaging studies and, possibly, liver biopsy. Even mild liver test abnormalities may be an early clue to the presence of potentially significant liver disease (Hay, J. E., et al., 1989). For instance, patients with chronic hepatitis C virus (HCV) infection are often asymptomatic unless they have advanced liver disease. They usually have mild elevation of the serum ALT level, and about one third have persistently normal liver enzyme levels. Accordingly, as mentioned above, lack of sensitivity and specificity limit the use of liver function tests. For example, in some clinical conditions (e.g., cirrhosis), patients may have serum aminotransferase levels in the normal to near-normal range. In addition, several nonhepatic factors (Moseley, R. H. 1996) can affect the results of tests that measure specific hepatic function, such as serum albumin, total bilirubin, and prothrombin time (PT).

Several markers have been proposed for cirrhosis and for pre-cirrhotic fibrosis, for example the serum levels of amino-terminal propeptide of procollagen type III (PIIINP) or the aminoterminal domain of procollagen type IV (PIVNP). However, abnormal serum levels may also be observed in non-hepatic diseases. In addition, these markers too are not very accurate, since in the case of PIVNP, about 40% of patients with cirrhosis and about 55% of patients with severe fibrosis show normal PIVNP levels (2).

The only reliable and definitive test for liver function and status is a biopsy. However, biopsies cannot be used in standard tests, or for patients with mild conditions or even for routine periodic analysis in patients with severe liver disease.

The human asialoglycoprotein receptor (ASGPR) is expressed only in hepatocytes and serves in the clearance of asialoglycoproteins from the plasma (3). ASGPR levels are much lower in developing liver than in fully developed liver. The receptor level is also reduced in patients with cirrhosis and dramatically down-regulated in hepatocarcinomas (4).

The ASGPR is constructed of two subunits of related amino acid sequence, H1 (46 kD) and H2 (50 kD). H2a and H2b are two alternatively spliced variants of the ASGPR H2 subunit (5). H2a differs from H2b only by the presence of an extra pentapeptide in the exoplasmic domain next to the membrane-spanning segment (5). It was shown that H2a is rapidly cleaved next to this pentapeptide to a 35 kDa fragment, comprising the entire ectodomain, which is secreted, constituting a soluble form of the receptor (sH2a) (6). Membrane-bound H2a does not participate in a receptor complex with H1 as is the case for H2b, and thus it is not a subunit of the receptor but a precursor for the soluble secreted form.

Although H2a is a type II transmembrane protein, indirect evidence suggests that signal peptidase is probably responsible for the cleavage to the soluble form. ASGPR sH2a was found to be efficiently secreted from the human hepatoma cell line HepG2 (6). It was discovered that when H2a is expressed in stably transfected NIH 3T3 cells it is also cleaved, however only about 30% of sH2a can be Golgi processed and secreted from transfected fibroblasts and the rest is degraded at the ER (6).

SUMMARY OF THE INVENTION

The background art does not teach or suggest an efficient non-invasive marker for liver disease, liver function or a marker for assessing the success of a liver transplantation.

The background art also does not teach or suggest antibodies, assays or kits which could be used to identify a non-invasive marker of liver disease, thereby enabling diagnosing and monitoring of such liver diseases.

The present invention overcomes these disadvantages of the background art by providing monoclonal antibodies capable of specifically binding to at least one epitope of the sH2a soluble marker protein. In addition, there are provided enabling assays, kits and methods of use thereof for testing liver function, diagnosing liver disease, monitoring liver disease, assessing liver function, monitoring the efficacy of treatment of liver disease, and monitoring and assessing the success of liver transplantation.

According to one aspect of the present invention, there is provided a monoclonal antibody or fragment thereof, capable of specifically binding to at least one epitope of sH2a. According to another aspect of the present invention, there is provided a monoclonal antibody or fragment thereof, specifically elicited by at least one epitope of sH2a.

According to features of the present invention, the at least one epitope comprises SEQ ID NO:1. According to still further features of the present invention, the monoclonal antibody or fragment thereof is described by deposit number, Cell Name—B9; Provisional Accession Number—04030801, which was done on Mar. 8, 2004 at the European Collection of Cell Cultures. According to further features of the present invention, the monoclonal antibody or fragment thereof comprises a chimeric antibody, a humanized antibody, a Fab fragment, a single chain antibody, an immobilized antibody or a labeled antibody.

According to another aspect of the present invention, there is provided a hybridoma cell line for producing a monoclonal antibody, comprising a cell line for producing the monoclonal antibody or fragment thereof described above. According to further features of the present invention, the hybridoma cell line is for producing a humanized monoclonal antibody or fragment thereof.

According to yet another aspect of the present invention there is provided a method for testing a sample from a subject, comprising detecting a level of sH2a in the sample.

According to features in the described preferred embodiments of the present invention, the testing comprises testing liver function in the subject, diagnosing a liver disease in the subject, monitoring a liver disease in the subject, monitoring the condition of the subject when the subject is after a liver transplantation, monitoring the efficacy of treatment for a liver disease given to the subject, staging cancer in the subject, staging fibrosis in the subject or quantitating the sH2a level in the sample.

According to yet further features in the described preferred embodiments of the present invention, the subject is a potential liver donor, and the testing comprises screening of the subject for detection of liver disease.

According to still further features in the described preferred embodiments of the present invention, the subject works with liver damaging agents, and the testing comprises screening of the subject for detection of liver disease.

According to the preferred embodiments of the present invention as described below, the sample comprises a serum sample, a plasma sample, a urine sample or a blood sample. According to features of the preferred embodiments the blood sample may comprise a whole blood sample or a blood fraction sample.

According to further features of the preferred embodiments of the present invention, the above method is performed using the monoclonal antibody or fragment thereof of the present invention. According to other features of the preferred embodiments described, the method may be performed using a polyclonal antibody, which preferably specifically binds SEQ ID NO:1 or 2, or is specifically elicited by SEQ ID NO:1 or 2.

According to a still another aspect of the present invention, there is provided a kit for detecting a level of sH2a in a sample of a subject, comprising an antibody or fragment thereof capable of specifically binding at least one epitope of sH2a.

According to features in the preferred embodiments of the present invention, the antibody further comprises a label.

According to additional features in the preferred embodiments of the present invention, the kit further comprising a control protein.

According to additional features in the preferred embodiments of the present invention, the sH2a protein level in the sample indicates a presence, state or absence of a liver disease in the subject.

According to an additional aspect of the present invention, there is provided a test kit for detecting a level of sH2a in a sample from a subject, comprising at least one antibody or fraction thereof, a solid phase for immobilizing a substance and an indicator for indicating the detected sH2a level in said sample.

According to features in the preferred embodiments of the present invention, the solid phase is for immobilizing the antibody or fragment thereof.

According to features in the preferred embodiments of the present invention, the at least one antibody or fragment thereof of the test kit comprises a polyclonal antibody, which preferably specifically binds SEQ ID NO:1 or 2 or is specifically elicited by SEQ ID NO:1 or 2.

According to further features in the preferred embodiments of the described present invention, the at least one antibody or fragment thereof comprises a monoclonal antibody, preferably the monoclonal antibody is as described in the present invention.

According to still further features in the preferred embodiments of the present invention as described, the kit further comprises one or more of a washing buffer, a blocking buffer and a sample dilution buffer. Preferably, the kit further comprises a printed matter, such that the printed matter contains instructions of use for the test kit.

According to still further features in the preferred embodiments of the present invention as described, the solid phase in the test kit comprises a test card carrying an immunological test strip, such that the antibody or fraction thereof of the kit is bound to the test strip.

According to still further features in the preferred embodiments of the present invention as described, the test kit further comprises a control protein, and the solid phase of the test kit is preferably a microtiter plate, such that the control protein is bound to the microtiter plate.

According to still further features in the preferred embodiments of the present invention as described, the test kit may be used in a physical location, including but not limited to a hospital, a clinic and a private home.

According to still further features in the preferred embodiments of the present invention as described, the test kit is used to perform the method described above.

According to yet an additional aspect of the present invention, there is provided an assay for diagnosing or monitoring a liver condition in a subject according to a sample from the subject, comprising at least one antibody or fragment thereof, a soluble marker protein in the sample and a reporter component for detecting presence or level of liver condition. Preferably, the liver condition is detected by quantification of a detected binding of at least one epitope of said soluble marker protein to said at least one antibody or fragment thereof. Preferably, the liver condition comprises liver disease.

In addition, according to a further aspect of the present invention, there is provided a kit for performing the described assay, comprising at least one antibody or fragment thereof, a soluble marker protein in a sample, a solid phase for immobilizing an antigen of the at least one antibody or fragment thereof and a reporter component for detecting presence or level of a liver condition.

According to yet a further aspect of the present invention, there is provided an assay for assessing the success of liver transplantation in a subject according to a sample from the subject, comprising at least one antibody or fragment thereof, a soluble marker protein taken from the sample and a reporter component for detecting the level of a soluble marker protein thereby enabling assessment of the success of transplantation. Preferably, the success of a liver transplantation is assessed by quantification of a detected binding of the soluble marker protein to the at least one antibody or fragment thereof.

In addition, according to still a further aspect of the present invention, there is provided a kit for performing the aforementioned assay comprising at least one antibody or fragment thereof, a soluble marker protein in a sample, a solid phase for immobilizing at least one epitope that binds the at least one antibody or fragment thereof and a reporter component for detecting the level of a marker protein thereby enabling assessment of the success of transplantation.

According to still a further aspect of the present invention, there is provided an assay for staging liver disease in a subject according to a sample from the subject, comprising at least one antibody or fragment thereof, a soluble marker protein in the sample and a reporter component for detecting the level of a marker protein thereby enabling staging of liver disease. Preferably, the staging of the liver disease is performed by quantification of the detected binding of the soluble marker protein to the at least one antibody or fragment thereof.

In addition, according to still a further aspect of the present invention, there is provided a kit for performing the aforementioned assay, comprising at least one antibody or fragment thereof, a soluble marker protein in a sample, a solid phase for immobilizing an antigen of the at least one antibody or fragment thereof and a reporter component for detecting the level of a marker protein thereby enabling staging of liver disease. Preferably the liver disease comprises liver cancer, liver fibrosis or liver cirrhosis.

According to still a further aspect of the present invention, there is provided an assay for monitoring the efficacy of a treatment for a liver disease in a subject according to a sample from the subject, comprising at least one antibody or fragment thereof, a soluble marker protein in the sample and a reporter component for detecting the level of the soluble marker protein thereby enabling monitoring the efficacy of said treatment.

In addition, according to still a further aspect of the present invention, there is provided a kit for performing the aforementioned assay, comprising at least one antibody or fragment thereof, a soluble marker protein in a sample, a solid phase for immobilizing an antigen of the at least one antibody or fragment thereof and a reporter component for detecting the level of a marker protein thereby enabling monitoring of the efficacy of a treatment for the liver disease.

According to still a further aspect of the present invention, there is provided an assay for quantitation of the level of sH2a in a sample, comprising at least one antibody or fragment thereof and a reporter component for detecting the quantity of sH2a.

According to features in the described preferred embodiments, the at least one antibody or fragment thereof of any of the above assays or kits comprises a polyclonal antibody. Preferably, the polyclonal antibody specifically binds SEQ ID NO:1 or 2 or the polyclonal antibody is elicited by SEQ ID NO:1 or 2.

According to further features in the described preferred embodiments the at least one antibody or fragment thereof of any of the above assays or kits comprises a monoclonal antibody. Preferably, the monoclonal antibody comprises an antibody as taught by the present invention.

According to still further features in the described preferred embodiments, the soluble marker protein of any of the above assays or kits is sH2a. Preferably, the liver disease of any of the above assays comprises liver cancer, liver fibrosis or liver cirrhosis. It should be noted that the term "soluble marker protein in the sample" may also optionally include such a soluble marker protein after partial and/or complete purification from the sample, and/or after removal from the sample.

According to still further features in the described preferred embodiments, the reporter component of any of the above assays comprises a suitable secondary antibody. Preferably, the suitable secondary antibody further comprises a label.

According to still further features in the described preferred embodiments, the label comprises an enzyme and the reporter component further comprises a substrate for the antibody. According to still further features in the described preferred embodiments, the label comprises a fluorescent moiety or a colorimetric moiety.

According to still further features in the described preferred embodiments, any of the above assays is for performing at least one of an ELISA, a flow through assay or an immunoblot. Preferably, the assay is for performing an ELISA. More preferably, the ELISA comprises a competitive ELISA.

According to still further features in the described preferred embodiments, any of the above kits further comprises one or more of a washing buffer, a blocking buffer and a sample dilution buffer.

According to still a further aspect of the present invention, there is provided a method of diagnosing a liver disease in a subject, the method comprising detecting a level of sH2a in a sample obtained from the subject, wherein the level of sH2a indicates a presence, state or absence of the liver disease thereby diagnosing the liver disease in the subject.

According to still a further aspect of the present invention, there is provided a method for monitoring a liver condition in a subject, the method comprising detecting a level of sH2a in a sample obtained from the subject, wherein said level of sH2a indicates the state of the liver condition. Preferably, monitoring the liver condition is performed several times at defined time intervals.

According to still a further aspect of the present invention, there is provided a method for monitoring the condition of a subject after a liver transplantation, the method comprising detecting a level of sH2a in a sample obtained from the subject, wherein said level of sH2a indicates the condition of the subject. Preferably, the condition of the subject after liver transplantation comprises recovery of the subject, lack of recovery of the subject, acceptance of the liver transplant in the subject or rejection of the liver transplant in the subject.

According to still a further aspect of the present invention, there is provided a method for staging liver disease in a subject, the method comprising detecting a level of sH2a in a sample obtained from the subject, wherein the level of sH2a indicates the stage of the disease in the subject.

According to still a further aspect of the present invention, there is provided a method for monitoring the efficacy of a treatment for a patient with liver disease, the method comprising detecting a level of sH2a in a sample obtained from the subject, wherein the level of sH2a indicates the efficacy of the treatment.

According to still a further aspect of the present invention, there is provided a method of quantitation of the level of sH2a in a sample, comprising obtaining a sample and performing the aforementioned assay of for quantitation of the level of sH2a in a sample on the obtained sample.

According to still a further aspect of the present invention, there is provided a method of diagnosing or monitoring a liver condition in a subject according to a sample comprising a soluble marker protein from the subject. The method comprising, (a) contacting the sample with an antibody or fragment thereof capable of specifically binding to the soluble marker protein, such that complexes comprising the soluble marker protein and said antibody or fragment thereof are formed; and (b) detecting level of the complexes in the sample, wherein the level is indicative of the presence or state of the liver condition, thereby diagnosing or monitoring the liver condition in the sample.

According to features in the described preferred embodiments, detecting the level is performed using an antibody or fragment thereof. According to further features in the described preferred embodiments, the at least one antibody or fragment thereof of any of the above methods comprises a polyclonal antibody. Preferably, the polyclonal antibody specifically binds SEQ ID NO:1 or 2 or the polyclonal antibody is elicited by SEQ ID NO:1 or 2.

According to further features in the described preferred embodiments the at least one antibody or fragment thereof of any of the above methods comprises a monoclonal antibody. Preferably, the monoclonal antibody comprises an antibody as taught by the present invention.

Preferably, the any of the described methods comprises measuring the deviation of the sH2a level in the sample in comparison to normal sH2a level or in comparison to a previously measured sH2a level.

According to still further features in the described preferred embodiments, the sample comprises a serum sample, a plasma sample, a urine sample, a whole blood sample or a blood fraction sample.

According to further features in the described preferred embodiments, the liver condition comprises a pathological condition of the liver, a dysfunction of the liver or a liver disease.

According to further features in the described preferred embodiments, the liver disease is selected from a group consisting of hepatocellular carcinoma, liver cirrhosis, liver fibrosis, and hepatitis. According to further features in the described preferred embodiments, the liver disease may be a genetic disease. Preferably, the genetic disease is selected from a group consisting of Wilson's disease, HHC and α-1-AntiTrypsin deficiency.

According to further features in the described preferred embodiments, liver fibrosis or cirrhosis is a result of alcohol abuse, of poisoning, of food poisoning, of hepatitis. Preferably, the hepatitis is viral. The liver fibrosis or cirrhosis may also be a result of an infection, bacterial or protozoal, a side effect of medical treatment such as treatment with statins, a result of drug abuse, a side effect of drug combination or a side effect of exposure to chemicals. The exposure to chemicals may be in a work place, at time of war in a terrorist act.

According to further features in the described preferred embodiments, the subject is human, or a fetus. According to still further features in the described preferred embodiments, the human is selected from a group consisting of Hepatitis B or C positives, HIV positives, bacterial or protozoal hepatitis carriers, patients receiving potential liver-damaging anesthetics, patients taking medicines with potential liver-damaging effects, cancer patients with potential metastasis, alcoholics, wine tasters, employees working with liver-damaging agents, victims of biological or chemical attacks in war, victims of terrorist acts, victims of poisoning and victims of food poisoning.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4a presents the results of positive and negative control experiments testing binding levels of a specific monoclonal anti-H2a antibody to a peptide bound to an ELISA plate after competition with another peptide, as would be used in an ELISA kit according to the present invention;

FIG. 4b presents the different binding levels of specific monoclonal anti-H2a antibodies to a peptide bound to an ELISA plate after being competed with different dilutions of human serum;

FIGS. 6a-b are graphs depicting ALT (FIG. 6a) and sH2a (FIG. 6b) levels in patient 1 with mild liver fibrosis along a period of 14 months. Samples of serum were taken before treatment with ribavirin and alpha-interpheron (first data point, No. 1) and at pre-determined times (in one month intervals) after treatment; No. 2=1 month post-treatment, No. 3=2 months post-treatment, No. 4=3 months post-treatment, No. 5=4 months post-treatment, No. 6=5 months post-treatment, No. 7=6 months post-treatment, No. 8=7 months post-treatment, No. 9=8 months post-treatment, No. 10=9 months post-treatment, No. 11=10 months post-treatment, No. 12=11 months post-treatment, No. 13=12 months post-treatment, No. 14=13 months post-treatment, No. 15=14 months post-treatment. 0.1 ml of serum were analyzed for ALT levels (FIG. 6a) or for sH2a (FIG. 6b) levels using the ELISA assay described under Materials and Experimental Methods. For ALT the levels were normalized by dividing by the values obtained for a sample of normal human serum (FIG. 6a). For sH2a the levels were normalized by dividing for those obtained for a sample of normal human serum and multiplied by 100 (% of normal) (FIG. 6b). Values were plotted as a function of time after treatment. The dashed lines indicate a level above which (for ALT) or below which (for sH2a) values are considered abnormal. Note the reduction upon therapy of ALT to normal levels in the serum of an HCV positive patient with mild liver fibrosis are followed by an increase of sH2a to its normal levels;

DESCRIPTION OF PREFERRED EMBODIMENTS

Figure 1:
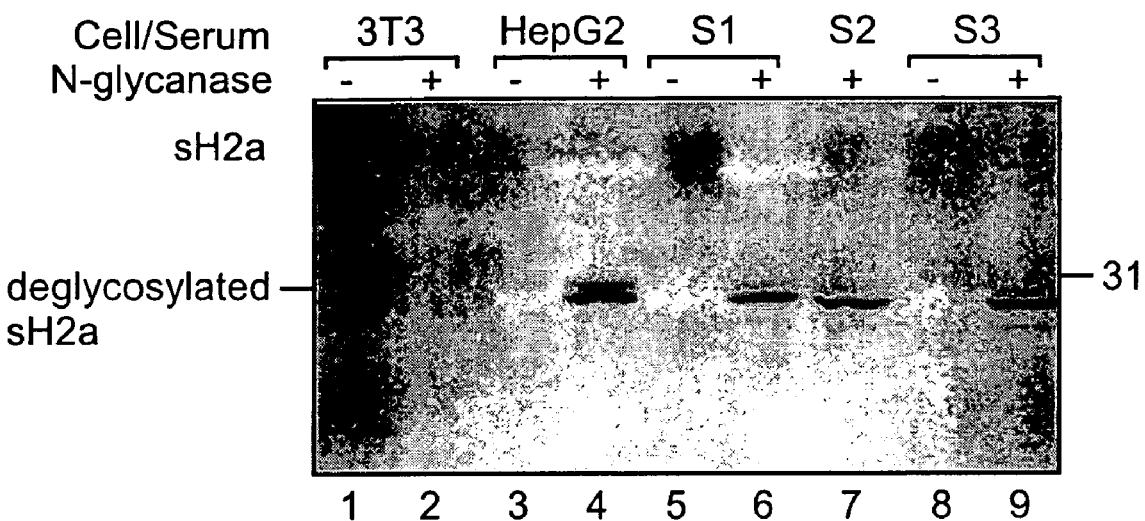
FIG. 1 demonstrates the level of sH2a in normal human serum (lanes 5-9) samples, in supernatant from HepG2 cells (lanes 3-4) and as a negative control in supernatant from untransfected 3T3 cells (lanes 1-2)

The present invention is of antibodies, kits, assays and methods of use thereof for a soluble non-invasive marker for liver function, liver disease, and for diagnosis of success in liver transplantation. Specifically, the present invention can be used to detect liver function, diagnose a liver disease or condition and monitor liver function.

The principles and operation of the methods and kits for detecting liver function according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Soluble secreted proteins that are expressed uniquely in specific organs, or proteins whose formation or secretion is regulated by disease states, are excellent markers for disease.

Various liver diseases such as viral infection with hepatitis B or C, liver fibrosis and cirrhosis which is an outcome of these viral diseases or arises from alcoholism or from non-alcoholic fatty liver disease (steatosis), hepatoma, hepatocellular carcinoma, metastatic liver cancer are among the major causes of death worldwide. In many cases, early detection and routine screening for abnormal liver function may reduce the fatalities associated with liver disease.

The gold standard for diagnosis of hepatomas is liver biopsy, but it cannot be performed on a routine basis, due to the invasiveness involved, and the complexity of the procedure.

Non-invasive serum markers may also be used for diagnosis, however in the case of liver cancer, the existing non-invasive serum markers are not satisfactory for the purpose of diagnosis, and even less suitable for early diagnosis of hepatomas.

The most established non-invasive tumor marker for hepatoma is α-fetoprotein that shows elevated levels following hepatocarcinogenesis. However, about 40% of the patients with small-sized hepatocarcinomas show normal α-fetoprotein levels (1).

Other markers which are generally included in a standard "liver function test" are mainly capable of assessing hepatocyte integrity, which might be indicative of severe liver damage, but do not reflect on the synthesis function of the liver.

Several markers have been proposed for cirrhosis and for pre-cirrhotic fibrosis, for example the serum levels of amino-terminal propeptide of procollagen type III (PIIINP) or the aminoterminal domain of procollagen type IV (PIVNP). However, abnormal serum levels may also be observed in non-hepatic diseases. In addition, these markers too are not very accurate, since in the case of PIVNP, about 40% of patients with cirrhosis and about 55% of patients with severe fibrosis show normal PIVNP levels (2).

While reducing the present invention to practice, the present inventors have uncovered that the level of the soluble form of the H2a polypeptide of the ASGPR is modulated in various liver conditions and diseases and therefore can be used as a marker for assessing liver function.

As is shown in Examples 1, 2, 5 and 9 of the Examples section which follows, sH2a level in the serum represent a sensitive marker for liver function in various conditions and diseases, including liver cancer, mild and moderate liver fibrosis, as well as following treatment of a liver disease.

Altogether, the findings of the present invention suggest the use of sH2a levels as powerful diagnosis tool for the determination of liver function. This is the first described true specific and sensitive test for liver function. It enables to assess liver function status in standard tests and diagnose the recovery of liver function in diverse liver diseases or after liver transplant. This diagnostic method can even replace the invasive technique used today as the gold standard for accurate assessment of liver function and disease, liver biopsy.

According to one aspect of the present invention, there is provided a monoclonal antibody or fragment thereof that specifically binds to at least one epitope of the soluble H2a receptor. In another aspect of the present invention, there is provided a monoclonal antibody or fragment thereof elicited by at least one epitope of sH2a. The monoclonal antibodies described above were raised against a H2 carboxyterminal peptide comprising SEQ ID NO:1 having the sequence CEKRRNATGEVA. The peptide was conjugated to a KLH protein, and was then used to immunize mice, as described in the Examples section below. Briefly, BALB/c mice were immunized with the carboxyterminal peptide of H2. Splenocytes from the mouse that acquired sufficiently high anitpeptide titers were fused with NS/O myeloma cells. The resulting hybridoma cells were then screened by ELISA, in order to select clones that reacted strongly with the peptide, but not with the carrying KLH.

A deposit of hybridoma cells of the present invention is maintained by ECACC (European Collection of Cell Cultures) (United Kingdom) since Mar. 8, 2004 under the following depository number: B9 04030801.

Access to this deposit will be available during the pendency of this application to persons determined by the US Commissioner for Patents to be entitled thereto under 37 CFR 1.14 and 35 USC 122, by the European Patent Office, or by any other national or regional patent office that is entitled to do so. Upon allowance of any claims in this application and/or publication of the application (as necessary), all restrictions on the availability to the public of the strain will be irrevocably removed by affording access to the deposit.

According to another aspect of the present invention, there is provided an assay for diagnosing a liver condition in a sample from a subject. According to yet another aspect of the present invention there is provided an assay for assessing the success of a liver transplantation, according to a sample from a subject. In another aspect of the present invention, there is provided an assay for monitoring the efficacy of a treatment for a patient with a liver disease. According to yet another aspect of the present invention there is provided an assay for staging liver disease, such as liver cancer, fibrosis and cirrhosis, in a patient. The assays preferably detect at least one selected protein in a sample from a patient, preferably the ASGPR, in its soluble form, otherwise known as sH2a. More preferably, the assays are quantitative or at least semi-quantitative, for detecting the level of sH2a in the sample from the patient. Although optionally any type of reporter may be used to detect the protein, preferably the reporter is an antibody or fragment thereof. Optionally the methods, assays and kits of the present invention may be used to discover people carrying a liver disease who are still presymptomatic or asymptomatic.

The assays optionally and preferably use at least one, and more preferably a plurality of antibodies or fragments thereof, specifically binding at least one epitope of sH2a, for detecting the presence of an immunological reaction to sH2a in the sample of the subject. The antibodies may be polyclonal or monoclonal. Preferably, the polyclonal antibodies may bind to either of the SEQ ID NO:1 or 2 (sequences CVTG-SQSEGHRGAQLQAE and CEKRRNATGEVA), and/or may be elicited by either of these sequences. Preferably, monoclonal antibodies are as taught previously in the present invention. More preferably, the quantity of sH2a is determined. Therefore, according to the present invention there is also provided an assay for quantitation of the level of sH2a in a sample, by quantifying the level of an immunological reaction to sH2a in the sample using at least one of the aforementioned antibodies.

Optionally and preferably, the subject is human and the immunological reaction detected features an antibody and a human polypeptide.

The immunological reaction may optionally be detected through the use of any suitable type of assay, including but not limited to, ELISA (enzyme-linked immunosorbent assay) or an immunoblot such as a Western blot for example, or a combination thereof. Preferably, competitive ELISA may be used. Another optional type of assay is a flow-through assay, as described below.

According to the preferred embodiment, diagnosis or monitoring of a liver condition, monitoring the efficacy of a treatment for liver disease, staging of liver cancer, fibrosis or cirrhosis and assessment or monitoring of success of liver transplantation, are effected by quantification of the detected immunological reaction, representing the quantity of the marker polypeptide (sH2a) in the sample.

In other preferred embodiments, the present invention also relates to test kits for detecting the level of a soluble marker protein in a sample thus enabling diagnosis or monitoring of a liver condition, monitoring of the efficacy of a treatment for liver disease, staging of liver disease, assessment of success of liver transplantation or monitoring the condition of a subject in which the transplantation was performed, which test kits contain at least one antibody or fragment thereof according to the invention, which is able to react with the marker polypeptide (sH2a) which is present in the fluid under investigation, and which contain at least one reporter component which makes it possible to detect complexes consisting of the antibody or fragment thereof and the soluble marker protein. The antibody may optionally be polyclonal or monoclonal, as described above.

Preference is given to test kits, which contain at least one monoclonal antibody or fragment thereof as described in greater detail above. The reporter component can be an antibody, which is directed against the antibody or fragment thereof which are used in the kit, and which exhibits a label. In this context, the reporter component is preferably a suitable IgG antibody or a suitable IgM antibody. The label is optionally and preferably an enzyme which is able to catalyze a color reaction, such as peroxidase for example, and is more preferably covalently bonded to the secondary antibody. Alternatively, the label may be a fluorescent moiety, or a colorimetric antibody.

In a preferred embodiment of the invention, the test kit is an ELISA test kit.

In a particularly preferred embodiment of the present invention, the ELISA test kit is a competitive ELISA test kit as described in the Examples section below. Preferably, at least one antibody or fragment thereof is preincubated with the sample which is investigated. Preferably, the antibody is monoclonal, and more preferably it is a monoclonal antibody according to the present invention as described above. The protein which was used to produce the anti-H2a antibody is coupled to microtiter plates as an exemplary solid phase (also referred to herein as a substrate), and the preincubated sample is then poured on the plate and the antibodies which were not previously bound to an epitope present in the sera can bind to the protein on the plate. The reporter component consists of a suitable immunoglobulin, in particular anti-IgG antibodies and/or anti-IgM antibodies, which can detect the antibody bound to the plate, and to which an enzyme which catalyzes a color reaction and/or a fluorescent label is coupled.

In another preferred embodiment of the present invention, the test kit is an immunoblot, which is also described as a protein blot or a Western blot. In test kits of this nature, protein from the sample is transferred, using an electrophoresis gel, for example a polyacrylamide gel, onto an immobilizing matrix (e.g. nitrocellulose filter). The transfer can be effected, for example, by means of electrotransfer. An immunological reaction then takes place between the proteins present on the matrix and the antibodies which are directed against the proteins. Preferably monoclonal antibodies or fragments thereof are used, and more preferably the monoclonal antibodies comprise antibodies according to the present invention as described above. The immunological reaction can then be detected by means of suitable methods, e.g. using enzyme-labeled and/or fluorescent-labeled anti-antibody antibodies.

In yet another preferred embodiment of the present invention, the test kit is for a flow-through assay. In kits for assays of this nature, an antibody or fragment thereof, is bound to a column, through which the tested sample is poured. The antibodies may be polyclonal or monoclonal as described above, and preferably the monoclonal antibodies used comprise antibodies according to the present invention as described above.

The tested sample is poured into the column, and flows through it. If the sample contains proteins which specifically bind to the antibodies or antibody fractions bound to the column, they will remain in the column and not flow through. Preferably, once all the sample fluid has passed through the column, the proteins bound to the column are washed out by flow of competing antibodies or by changing the buffering conditions. Preferably, if different proteins bind to the column they will be washed out at different phases. The quantity of the proteins obtained from washing the column or found in a specific phase of the column wash is then measured. Techniques for quantification of purified soluble proteins are well known in the art, for example by measuring the optical density of the fluid containing the proteins.

In a further preferred embodiment of the present invention, there is provided a test kit for ascertaining the level of sH2a in a sample taken from a subject, wherein a binary indicator indicates whether sH2a level is in a normal level, or below normal level. Preferably, the sample taken from the subject is a fluid sample. The test kit preferably includes a container for holding the sample fluid, an antibody or fragment thereof, and an indicator. Preferably, the antibody is monoclonal, and more preferably it is a monoclonal antibody according to the present invention as described above. Optionally and preferably the kit further includes solutions and buffers necessary for performing the test, and a printed matter optionally containing instructions for performing the test and interpreting the results. The test kit may be used by those who are not skilled in the art, and may be used in any physical location including but not limited to hospitals, clinics and private homes.

In one preferred embodiment of the present invention, the antibodies included in the test kit are bound to at least one immunoassay test strip, which may in turn be bound to a card type member. Preferably, the test strip is reactive to provide a visual indication in response to sH2a levels which are below normal. The test card thus provides for the detection of abnormal levels of sH2a, and therefore in detection or monitoring of liver disease as described above. Optionally and preferably the indicator is a color indicator, such that when the sH2a level in the sample is abnormal, the indicator shows one color, and when the level is normal a different color is presented by the indicator. Optionally, one of the indicating colors may be the original color of the test strip. According to a preferred embodiment, the container is used to collect the sample, and the test card holding the test strip is dipped into the container, for an amount of time sufficient for allowing an immunological reaction to occur. The test card is then removed from the container, and analyzed visually to ascertain the test results, preferably according to the exemplary printed matter. For example, the test strip is originally white, and after being dipped in the sample for sufficient time, a colored (for example blue or red) line appears in the dipped area. This result may be indicative of a low sH2a level, which should be accompanied by medical care. If however, the test strip obtains a different color, or remains white, the sH2a level may be considered as normal.

In another preferred embodiment of the present invention, the binary test kit is a simplified ELISA assay kit. According to this embodiment, there is provided a solid phase such as a microtiter plate, and a control protein bound to the solid phase. The obtained sample is preincubated with the antibodies or fragments thereof of the kit, for a time period sufficient for the occurrence of an immunological reaction. The mixture of sample and antibodies is then preferably poured on the plate allowing any unbound antibodies bind to the proteins on the plate. Use of the indicator then visually indicates what quantity of antibodies bound to the plate, which in turn indicates the quantity of sH2a in the sample. The indicator in this embodiment may be a secondary antibody, that catalyzes a color reaction. For example, assuming that the sample poured onto the plate is originally substantially clear, if the fluid in the plate turns colored, for example blue, there is an indication of strong immunological reaction in the plate, indicating low sH2a levels in the sample. If however, the fluid in the plate remains substantially clear, this is indicative of normal sH2a levels in the sample.

The term "test kits" or "kit", which is interchangeably used herein, is understood as meaning a set of test reagents which makes it possible to detect particular protein or proteins. The test kits according to the present invention contain, as the component according to the invention, at least one antibody or fragment thereof, preferably a monoclonal antibody and more preferably according to the invention. The antibody or fragment thereof immunologically reacts with a protein containing an antigen for the protein and which is present in the sample, such as a fluid, under investigation. The test kits according to the invention can optionally be based on various principles which are known per se. As a rule, a reaction takes place between the antigen and antibodies and this reaction, or the complex which is formed in this context, is detected and preferably quantified. It is possible for a positive control antigen to be bound to a solid phase such as a microtiter plate or magnetic beads. This antibody or fragment thereof can then be brought into contact with the fluid under investigation (for example serum, plasma, urine, whole blood or any type of blood fraction). The antigens which are present in the fluid under investigation then bind to the antibody. A wash is then optionally but customarily performed, after which the bound antibodies are detected by means of quantification of the antibodies bound to the solid phase by suitable secondary antibodies which carry a label. The label can be a radioactive isotope or an enzyme which catalyzes a color reaction, for example horseradish peroxidase, and/or a fluorescent label. The secondary antibody may optionally be biotinylated. The complex is then detected by adding avidin to which a color reaction-catalyzing enzyme, for example, is coupled.

Within the context of the present invention, a preferred embodiment features test kits which are suitable for implementing an ELISA (enzyme-linked immunosorbent assay), a flow through assay as described herein or for implementing a Western blot. Preferably, the ELISA assay comprises competitive ELISA.

An ELISA method, assay and kit according to the present invention were developed based on polyclonal antibodies, and another was based on the monoclonal antibodies taught above. In a clinical trial normal human serum samples and samples from patients with liver disease such as cirrhosis and fibrosis were screened with the kit according to the present invention, as described in greater detail below. The kit was able to detect, with high sensitivity, the level of sH2a in the different samples, which was substantially lower in patients with liver disease, and which recovered to normal levels in patients after treatments or in patients after successful liver transplantation. Therefore, the kit according to the present invention was useful for detecting liver disease in a patient even from early stages of the illness, or for assessment of the success of liver transplantation. Currently, the diagnosis of liver disease is mainly based on liver biopsy, as described herein above. Thus, the present invention has a clear advantage of providing a useful kit, which can accurately and in a non-invasive manner diagnose liver disease, and success or failure of liver transplantation. As shown with more detail in the Examples section below, the present invention is the first to provide a soluble marker protein which is a consistent, reliable indicator of liver function, as well as assays, kits and methods of use thereof.

As used herein, the phrase "liver function" refers to a function of the liver, including, but not limited to, protein synthesis such as serum proteins [e.g., albumin, clotting factors, alkaline phosphatase, aminotransferases (e.g., alanine transaminase, aspartate transaminase), 5'-nucleosidase, gamma.-glutaminyltranspeptidase, etc.], synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; excertion function of cholesterol, bile acids, phospholipids and bilirubin; and a hemodynamic function, including splanchnic and portal hemodynamics.

As described above, in the case of a liver disease there is a change in the level of sH2a in the serum. Therefore, liver disease can be detected and monitored by using the antibodies, assays and kits of the present invention. The assays and kits of the present invention may also be used for testing presymptomatic or asymptomatic individuals, or individuals with no overt symptoms, and thus can enable treatment even before symptoms of the disease appear. Optionally, discovery of low levels of sH2a in a sample tested according to the present invention may be used as a marker for starting treatment, regardless of the appearance of symptoms, as low sH2a levels indicate a developing liver disease. This may be useful for better screening of the population in a case of endemic diseases. Thus, according to a further aspect of the present invention, there is provided a method of diagnosing a liver disease in a subject or for monitoring a liver disease in a subject, the method comprising detecting the level of sH2a in a sample obtained from the subject, wherein the level of sH2a indicates a presence, state or absence of the liver disease, thereby diagnosing or monitoring the liver disease in the subject. Diagnosis and monitoring are achieved by measuring the deviation of the level of sH2a detected in the obtained sample, in comparison to the level in a normal sample or to a previously measured level of sH2a, as described in the Examples section below. In the case of monitoring a disease, optionally and preferably the level of sH2a is detected a plurality of times, at defined intervals as determined by one of skill in the art. In addition, the method can optionally be used to monitor a dysfunction of the liver, or another pathological condition of the liver.

In a preferred embodiment of the present invention, the level of sH2a is detected using antibodies, which may be monoclonal or polyclonal, and preferably are the monoclonal antibodies taught by the present invention. Preferably, detection and diagnosis are performed using the taught assay and kit of the present invention, as described above. According to further preferred embodiments of the present invention the subject that is diagnosed is a human, and the sample is a fluid sample, optionally and preferably a sample of serum, urine, plasma, whole blood or any type of blood fraction.

The liver disease which is detected or monitored can be hepatocellular carcinoma, liver cirrhosis, liver fibrosis and hepatitis.

The phrase "liver fibrosis" refers to the growth of scar tissue in the liver due to any of a variety of chronic toxic insults, including, but not limited to, chronic alcohol abuse; chronic exposure to drugs (e.g., acetominophen, amiodarone, aspirin, azathioprine, isoniazid, methyldopa, methotrexate, mitrfurantoin, propylthiouracil, and sulfonamides); chronic exposure to certain chemical agents (e.g., carbon tetrachloride, dimethyl nitrosamine, vinyl chloride, polychlorinated biphenyls, aflatoxins, and pesticides); infection with Schistosoma mansoni; diabetes; autoimmune disorders (e.g., primary sclerosing cholangitis, primary biliary cirrhosis, autoimmune hepatitis, lupoid hepatitis), and inflammatory bowel disease; hemochromatosis; alpha-1-antitryrsin deficiency; chronic cholestatic hepatitis; non-alcoholic steato-hepatitis; chronic biliary obstruction; Wilson's disease; and other conditions known to cause cirrhosis.

Liver cirrhosis is a degenerative condition in which the liver parenchyma deteriorates, the lobules are infiltrated with fat and dense perilobular connective tissue are formed. As a result, the blood supply to the remaining cells is reduced leading to portal hypertension and eventually death.

As described above, fibrosis and cirrhosis can result from several situations, including but not limited to alcohol abuse, poisoning, food poisoning, side effects of medical treatments such as treatment with cholesterol lowering drugs like statins, drug abuse, side effects of drug combination, drugs that metabolize into liver damaging agents, side effects of exposure to chemicals such as in a work place, at time of war or in a terrorist act, hepatitis including viral hepatitis, a bacterial or protozoal infection, and liver failure, including acute and fulminant hepatic failure for example. Examples of statins include but are not limited to, simvastatin, lovastatin, mevastatin, pravastatin, fluvastatin, atorvastatin, cerivastatin, and pitavastatin. However, it should be noted that other drugs and/or drug combinations may also cause liver damage, fibrosis and/or cirrhosis.

Due to the many possible causes for liver cancer, fibrosis and cirrhosis, many people are in danger of developing these diseases, and should be tested for early detection or monitoring of the diseases. People in danger of developing liver disease are selected from a group including but not limited to Hepatitis B or C positives, HIV positives, bacterial or protozoal hepatitis carriers, patients receiving potential liver-damaging anesthetics, patients taking medicines with potential liver-damaging effects (e.g. cholesterol-lowering drugs such as statins), cancer patients with tumors in other organs, alcoholics and wine tasters, employees working with liver-damaging agents, victims of biological or chemical attacks in war or terrorist acts and victims of poisoning or food poisoning, as well as patients who may be particularly sensitive to drugs having effects on the liver, including but not limited to, the elderly and children (both of whom have lower metabolic capabilities for metabolizing drugs in the liver), and/or patients with reduced liver function, and/or patients receiving multiple drug treatments which may interact in terms of liver metabolism, particularly in patients who are already at some risk (such as those patients in the previous categories for example). The antibodies, methods, kits and assays taught in the present invention may be used for monitoring the condition of all the aforementioned individuals.

In addition, there are some genetic diseases, such as Wilson's disease, HHC, and alpha-1 AntiTrypsin deficiency ($\alpha$-1AT), that cause the liver to dysfunction, and may cause cirrhosis or chronic hepatitis. As of yet, no single test may be used to diagnose or monitor the development of Wilson's disease. The present invention may be used to monitor patients carrying mutations for this disease, and may possibly also be used for prenatal genetic testing and diagnosis, and may also be used in gene therapy. Therefore, according to a further preferred embodiment of the present invention, monitoring or diagnosing liver disease in a subject preferably includes monitoring and diagnosing liver disease caused by a genetic mutation. Optionally and preferably, the subject may be a fetus, when using the method as a diagnostic tool in prenatal genetic testing.

As the level of sH2a was shown to be low also in patients before a liver transplantation, and to rise back to normal levels as the transplant is accepted and the patient recovers, the antibodies, assays and kits of the present invention may be used for monitoring the condition of a subject after a liver transplantation. Therefore, there is provided a method for monitoring the condition of a subject after a liver transplantation, again by detecting a level of sH2a in a sample obtained from the subject, wherein said level of sH2a indicates the condition of the subject. The method may optionally and preferably be performed by applying the assay for assessing success of a liver transplantation as described above. As described above, for accurate monitoring of a condition sH2a levels must be detected a plurality of times at intervals defined by one of skill in the art, and detection is performed by measuring the deviation of the sH2a level in the sample in comparison to the level detected in normal serum or in a previously measured sample.

In addition, as the assay of the present invention may be used for testing presymptomatic or asymptomatic individuals and individuals with no overt symptoms, the assays, kits and methods of the present invention may be used to screen potential liver donors, thus substantially ensuring transplantation of a healthy liver.

According to the preferred embodiments of the present invention, the monitored condition is selected from a group consisting of, but not limited to recovery or lack thereof of the subject, acceptance of the liver transplant and rejection of the transplant.

As described in further detail in the Examples section below regarding liver cancer, and without wishing to be limited to a single hypothesis, it is thought that upon de-differentiation of liver cells into malignant cells, there is a reduction in the production and secretion of sH2a from hepatocytes. However, before de-differentiation, at the first stages of tumor development, neoplastic expansion of hepatocytes could lead to increased secretion of sH2a, as seen in lane H5 of FIG. 2. Therefore, there is provided a method according to the present invention for staging liver disease in a subject, by measuring the sH2a level in a sample obtained from the subject, and defining the deviation of the detected level from the normal sH2a level. The method is preferably performed using any of the antibodies fragment thereof of the present invention as described above.

In addition, there is provided a method for monitoring the efficacy of a treatment for a patient with liver disease, by detecting the level of sH2a substantially as described above. This is possible since the level of sH2a returns to its normal high when a patient recovers from a liver disease, as shown in the Examples section below.

Moreover, there is provided a method for monitoring the effects and/or side effects of different drugs or drug combinations, by detecting the level of sH2a substantially as described above. Optionally, the effecting drugs are statins, which were found to lower cholesterol levels, but were also shown to have side effects on liver function. Other possible drugs that may affect the liver are drugs that metabolize into toxins during metabolism cause toxic intermediates and/or metabolic products to be formed in the liver. Not wishing to be limited to a single hypothesis, such metabolizing drugs may have an extreme effect on the liver as that is the physical location of degradation, detoxification and metabolism of substances, and the first organ to contact the resulting toxin. The side effects to the liver by such drugs should specifically be monitored in pediatric and geriatric patients, as these patients are more prone to the effects of such drugs, as previously described.

According to another aspect of the present invention there is also provided a method for quantitation of sH2a levels in an obtained sample, by using the quantification assay described above on the obtained sample.

According to the preferred embodiments of the present invention, the monoclonal antibodies of the present invention can be chimeric antibodies, humanized antibodies, Fab fragments, single-chain antibodies, immobilized antibodies and labeled antibodies.

The term "antibody" as used to describe this invention includes intact molecules as well as functional fragments thereof, such as Fab, F(ab')$_2$, Fv and scFv that are capable of specific, high affinity binding to a human major histocompatibility complex (MHC) class I complexed with a HLA-restricted antigen. These functional antibody fragments are defined as follows:

(i) Fab, the fragment which contains a monovalent antigen-binding fragment of an antibody molecule, can be produced by digestion of whole antibody with the enzyme papain to yield an intact light chain and a portion of one heavy chain;

(ii) Fab', the fragment of an antibody molecule that can be obtained by treating whole antibody with pepsin, followed by reduction, to yield an intact light chain and a portion of the heavy chain; two Fab' fragments are obtained per antibody molecule;

(iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds;

(iv) Fv, defined as a genetically engineered fragment containing the variable region of the light chain and the variable region of the heavy chain expressed as two chains; and (v) scFv or "single chain antibody" ("SCA"), a genetically engineered molecule containing the variable region of the light chain and the variable region of the heavy chain, linked by a suitable polypeptide linker as a genetically fused single chain molecule.

Methods of making these fragments are known in the art. See for example, Harlow and Lane, Antibodies: A Laboratory Manual, Cold Spring Harbor Laboratory, New York, 1988, incorporated herein by reference.

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73:119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2:97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

Humanized forms of non-human (e.g. murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence.

The humanized antibody optimally also will comprise at least a portion of an immunoglobulin constant region (Fc), typically that of a human immunoglobulin [Jones et al., Nature, 321:522-525 (1986); Riechmann et al., Nature, 332: 323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

It will be appreciated that once the CDRs of an antibody are identified, using conventional genetic engineering techniques can be used to devise expressible polynucleotides encoding any of the forms or fragments of antibodies described herein. As described above, the antibodies taught by the present invention may be used for diagnosis of a liver disease, or for assessment of success of a liver transplantation.

Several approaches well known to one of ordinary skill in the art can be used to apply the teachings, such as an antibody kit utilizing the antibody described herein conjugated to a detectable moiety (e.g. fluorescent moiety) can be used to assess the levels of the sH2a marker in a blood serum sample obtained from a tested individual and thus determine the presence/absence or even state of the disease.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion.

Materials and Methods

Materials: Immobilon-P paper was purchased from Millipore Corp. (Bedford, Mass.). Protein A-sepharose was purchased from Repligen (Cambridge, Mass.). N-glycosydase F was obtained from Boehringer Mannheim Biochemicals (Indianapolis, Ind.). Succinimidyl 4-(N-maleimidomethyl)cyclohexane-1-carboxylate (SMCC) was purchased from Pierce (Rockford, Ill.). A solution of 3,3',5,5'-tetramethylbenzidine (TMB) was purchased from Kirkegaard and Perry Laboratories Inc. (Gaithersburg, Md.). Other common reagents were purchased from Sigma Chem. Co. (St. Louis, Mo.).

Conjugation of peptide to carrier: The immunizing peptide (H2 carboxyterminal peptide (SEQ ID NO. 1 or CEKRRNATGEVA) or a synthetic peptide including 18 residues from the juxtamembrane ectodomain of H2a (SEQ ID NO. 2 or CVTGSQSEGHRGAQLQAE)) was coupled to KLH using succinimidyl 4-(N-maleimidomethyl)cyclohexane-1-carboxylate (SMCC). 10 mg of KLH was dissolved in 0.75 ml PBS (Phosphate Buffered Saline (PBS): 10 mM Phosphate buffer pH 7.4, 150 mM NaCl) and mixed gently with 1.8 mg SMCC dissolved in 0.2 ml of dimethylformamide. The mixture was incubated at RT for 30 minutes after which 4 ml of 0.1 M NaPO4 pH 6 were added. The solution was loaded onto a column of Sephadex G-25 equilibrated in 0.1 M NaPO4, pH 6. Fractions of ~1 ml were collected and protein concentration was determined using the Bradford method. Peak protein/crosslinker fractions (~5 ml) were taken, mixed with 5 mg peptide dissolved in 1 ml 0.1 M NaPO4 pH 6 and incubated overnight at RT. The conjugate was then dialyzed against 4 liters of PBS at 4° C.

Polyclonal Antibodies: Polyclonal antibodies specific for a peptide corresponding to the carboxyterminus of H2a or to a peptide unique to H2a (anti-H2a) were produced as described in earlier studies (6).

Briefly, anti-H2a pentapeptide antibodies were raised in rabbits against a synthetic peptide including 18 residues from the juxtamembrane ectodomain of H2a, SEQ ID NO. 2 or CVTGSQSEGHRGAQLQAE. For immunizing the rabbits, the peptide was coupled to the carrier protein keyhole limpet hemocyanin (KLH) with sulfosuccinimidyl 4-(N-maleimidomethyl)cyclohexane-1-carboxylate as described above. The same procedure was used to prepare anti-H2 carboxyterminal antibodies but using the synthetic peptide comprising SEQ ID NO 1 or CEKRRNATGEVA.

Monoclonal antibodies: BALB/c mice were immunized intraperitoneally with 30 micrograms of a conjugate of KLH with the carboxyterminal peptide of H2 (SEQ ID NO 1CEKRRNATGEVA) and complete Freunds adjuvant. Three boosts were then performed intraperitoneally, each with 30 micrograms of conjugate with addition of incomplete Freunds adjuvant and finally an intravenous boost with 30 migrograms of conjugate without adjuvant. The splenocytes of the mice that acquired relatively high anti-peptide titers were then fused according to (Galfre, G., Milstein, C. (1981). Preparation of monoclonal antibodies: strategies and procedures. Methods Enzymol. 73: 3-46) except that NS/O myeloma cells were used as the immortal partner. The resulting hybridoma cells were screened by ELISA against the peptide and against KLH, selecting clones that reacted strongly with the peptide but not with the carrier. One such clone was found and was analyzed using an Isotype Test kit, Isostrip, Roche diagnostic corporation, cat No. 1493027. According to the test the isotype was found to be IgG3. Hybridoma cells were injected to mice and ascitic fluid was collected. Due to difficulties in IgG3 purification by standard methods, non-purified ascitic fluid was used in all experiments. It did not show any significant background.

Immunoprecipitation: Immunoprecipitations from cell supernatants (1.2 ml from 60 mm dishes) were performed directly by addition of 2 mM PMSF, protein A-sepharose and anti-H2a carboxyterminal antibodies, followed by incubation at 4° C. with rotation for 4-16 hours. Immunoprecipitations from serum samples (200 µl) were performed in a similar manner, using anti-H2a antibodies crosslinked to protein A-sepharose with dimethyl pimelimidate. Washes of the immunoprecipitates, treatment of immunoprecipitates with N-glycosidase F and SDS-PAGE were performed as described in previous studies (6).

Briefly, for treatment with N-glycanase, immunoprecipitates were washed and then boiled in 10 µl of 0.5% SDS in 50 mM sodium citrate, pH 6.0. Then, 10 µl of a solution containing 200 mM sodium phosphate, pH 8.0, 40 mM EDTA, pH 8.0, 3% N-octylglucoside was added, together with 40 milliunits of N-glycanase, and incubations were carried out overnight at 37° C. Twenty µl of sample buffer were added and the samples boiled before loading for SDS-PAGE. SDS-PAGE was performed on 10% Laemmli gels except where stated otherwise. The gels were analyzed by fluorography using 20% 2,5-diphenyloxazole and quantitated by densitometry as described previously (6).

Protein transfer and Immunoblotting: Proteins were transferred to a nitrocellulose membrane. Blocking was performed using 5% low fat milk and 0.1% Brij-35 in PBS for 2 hours at room temperature. Blocking was followed by incubation overnight at 4° C. with the primary antibody. The blot was then washed 3 times in PBS containing 0.1% Brij-35 and incubated for 60 minutes at room temperature with goat anti-rabbit IgG conjugated to peroxidase (Jackson) at 0.27 µg/ml. The blots were washed 4 times with 0.1% Brij-35 in PBS, and once with PBS, after which detection was performed using a commercial TMB solution (Kirkegaard and Perry Laboratories Inc. (Gaithersburg, Md.) "TMB Peroxidase Substrate" solution Cat. No. 50-76-01 and "Peroxidase Solution B" Cat. No. 50-65-00) and the blot was photographed. Alternatively, detection was performed by the ECL procedure, using a freshly prepared solution of 2.5 mM Luminol, 400 mM paracoumaric acid in 100 mM Tris-HCl, pH 8.5 mixed with 5.4 mM $H_2O_2$ in 100 mM Tris-HCl pH 8.5 and exposed to Agfa CP-BU film.

Competitive ELISA: Corning ELISA plate wells were coated with the carboxyterminal peptide of H2 (5 µg/ml) and blocked with 3% BSA. Ascitic fluid containing anti-peptide monoclonal antibody (1:1000) was preincubated overnight at 4° C. with 8 double dilutions of the serum sample. It was then added to the coated ELISA plate wells and incubated for 1 hour at RT. The wells were washed with TBS (154 mM NaCl in 10 mM Tris-HCl, pH 7.5) and reacted with goat anti-mouse IgG conjugated to alkaline phosphatase (Jackson, 1:2500 in 0.3% BSA in TBS) for 1 hour at RT. After adding an alkaline phosphatase substrate (p-nitro phosphate (p-NPP), 100 µl per well, cat. No. ES009-500 mL Chemicon International (Temecula, Calif.)) the OD was quantified using an ELISA reader at a wavelength of 410 nm.

Example 1

Detection of sH2a in Human Sera

As mentioned above, it has been previously shown that ASPGR is secreted from the Human Hepatoma cell line HepG2 cells. However, in order to find out the physiological relevance of the soluble form of the receptor it was important to know whether it is also secreted from normal hepatocytes.

A mixture of monoclonal anti-ASGPR antibodies was previously reported to reveal immunoreactive bands on a Western blot containing samples of human serum (8). Although that report does not elucidate whether the detected bands were representative of H1, H2a or H2b, the molecular weight of ~40 kDa is consistent with the found mass of the secreted H2a fragment. An experiment was performed in order to ascertain the presence or lack thereof of secreted ASPGR in normal human sera samples, as described below.

Experimental Methods 1.2 ml cell supernatants from 90 mm petri-dishes of 3T3 (lanes 1-2) or HepG2 (lanes 4-5), or 0.3 ml of normal human sera from 3 donors (S1, lanes 5-6; S2, lane 7; S3, lanes 8-9) were immunoprecipitated with anti-H2 carboxy-terminal antibodies and subjected to 12% SDS-PAGE. The proteins were then transferred to a nitrocellulose membrane and the blot was reacted with the anti-H2 carboxy-terminal antibody, followed by goat anti-rabbit peroxidase. The detection of the bands was performed using the TMB membrane peroxidase substrate (3,3', 5,5'-tetramethylbenzidine). Samples in lanes 2, 4, 6, 7 and 9 were treated with N-glycanase after immunoprecipitation. All the methods were performed substantially as described in the materials and methods section above.

Experimental Results

FIG. 1 shows the results of the described experiment. On the right is the molecular weight of a protein standard in kilodaltons. On the left the positions for migration of sH2a before or after deglycosylation are indicated.

In lanes 6-7 and 9, that represent normal human sera samples, the presence of a band of about 28 kDa is detected. The band is the same size as the one found for sH2a in media from HepG2 cells, as seen in lane 4. Lanes 3, 5, and 8 were not treated with N-glycosidase F, and show a disperse band of about 40 kDa. It is clear from the results that sH2a is indeed present in normal human sera. The presence of H1 in normal human serum was also analyzed and none was detected (results not shown).

Example 2

Downregulation of Serum Levels of sH2a in Liver Cancer

Experimental Methods 0.1 ml of sera from 8 samples was immunoprecipitated with anti-H2 carboxy-terminal antibody and treated with N-glycanase. The samples were run on 12% SDS-PAGE. The gel was blotted and the blot was reacted with the anti-H2 antibody followed by goat anti-rabbit peroxidase. The detection was performed by the ECL procedure. All the methods were preformed substantially as described above in the materials and methods section.

Five of the samples were taken from patients with liver cell carcinoma (H1-H5), one was taken from a patient after liver transplantation (H6), two samples were taken from healthy individuals (N1-N2), and one was cell supernatant of HepG2 cells (HepG2).

Experimental Results

Figure 2:
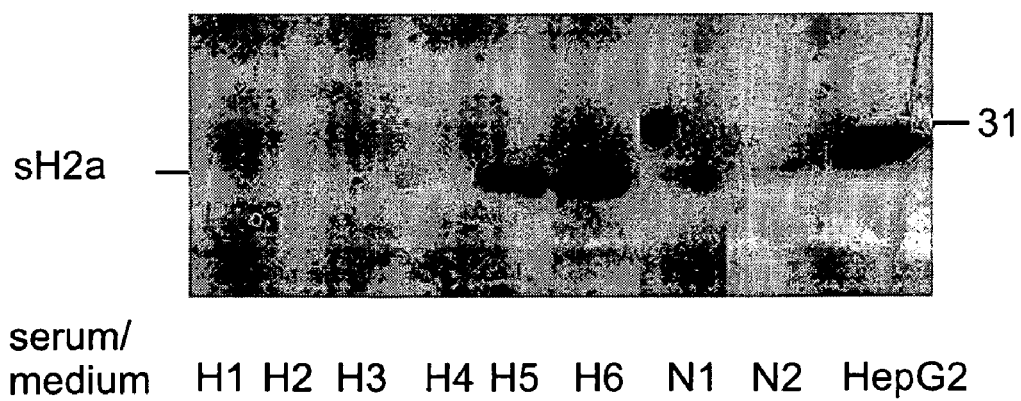
FIG. 2 presents the different levels of sH2a in normal human sera and in serum from patients with hepatocarcinoma. Lanes H1-H5 contain samples from patients with hepatocarcinoma, lanes N1-N2 contain normal human serum, lane HepG2 contains HepG2 cell supernatant and lane H6 contains serum from a subject after liver transplantation.

As can be seen in FIG. 2, similar amounts of sH2a were found in several normal human sera tested (lanes N1, N2). However, the sH2a level was much reduced in sera from patients with liver cell carcinoma (lanes H1-H5), although there is one sample that showed an increase in sH2a level (lane H5). A high level of sH2a was found in the serum of a patient after liver transplantation (lane H6).

Without wishing to be limited to a single hypothesis, it is thought that upon de-differentiation into malignant cells, there is a reduction in production and secretion of sH2a from hepatocytes. However, before de-differentiation, neoplastic expansion of hepatocytes could lead, as a first stage, to increased secretion of sH2a, as seen in lane H5 of FIG. 2.

It is clear that sH2a may be used as a non-invasive marker for liver disease and for success of liver transplantation, since distinct levels of the protein are found in different samples and different conditions.

Example 3

ELISA Assay Using Polyclonal Antibodies in Order to Quantitate Serum Levels of sH2a Experimental Methods 5 µg/ml of a peptide from H2a that was used to produce the anti-H2a antibody in rabbits was incubated for 2 hours to immobilize it on an ELISA plate. The plate was then reacted with anti-H2a serum [1:2000 in 0.3% BSA in TBS (154 mM NaCl in 10 mM Tris-HCl, pH 7.5)] that had been preincubated with normal human sera (N1-N3) or with sera from hepatocarcinoma patients. The plate was then incubated with 0.08 µg/ml of goat anti-rabbit antibodies conjugated to HRP in 0.3% BSA in TBS, and reacted with 0.4 mg/ml o-phenylenediamine (Sigma P-6787) in 500 mM phosphate-citrate buffer, pH 5 (Sigma, P4809). The developed color was then quantified in an ELISA reader spectrophotometer.

Experimental Results

Figure 3:
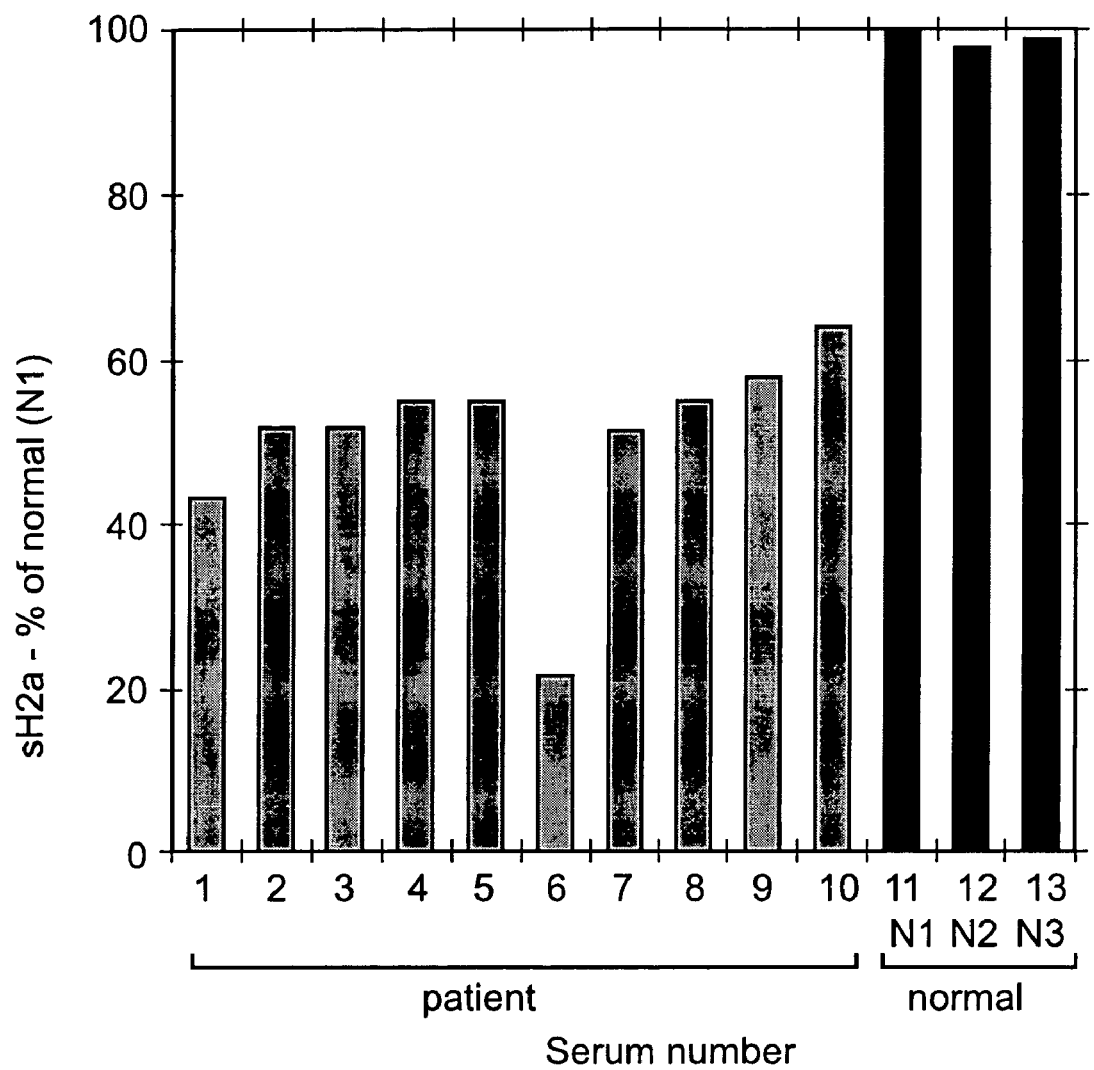
FIG. 3 presents a comparison between the level of sH2a in normal human serum and in serum taken from patients. On the left is indicated the percentage of the protein level in comparison to one of the normal samples (N1)

In order to obtain a quantitative measure of the concentration of sH2a in serum and for better comparative analysis, an ELISA assay was developed. The assay is based on the binding of an affinity purified polyclonal anti-H2a peptide antibody to its peptide. Binding could be competed by preincubation of the antibody with a solution containing the same peptide, but not with a control peptide. The binding could also be competed in a concentration dependent manner, by preincubation of the antibody with normal human serum. Undiluted serum showed 57% inhibition of the binding. Analysis of samples of normal human sera show a very constant level of sH2a, which was much reduced in sera from hepatocarcinoma patients. FIG. 3 shows sH2a levels in several individuals expressed as percent of a normal serum (N1).

Example 4

ELISA Assay Using Monoclonal Antibodies in Order to Quantitate Serum Levels of sH2a The ELISA assay described above in Example III was improved by developing a new specific monoclonal anti-H2a antibody that binds specifically to the same carboxyterminal peptide as the polyclonal antibody used above. The antibody was developed as described above in the Materials and Methods section.

Experimental Methods

5 µg/ml of H2a carboxyterminal peptide was incubated for 2 hours on an ELISA plate in order to immobilize it. The plate was then reacted with ascitic fluid containing anti-peptide monoclonal antibody (1:1000) for 1 hour at RT. The wells were washed with TBS and reacted with goat anti-mouse IgG conjugated to alkaline phosphatase. An alkaline phosphatase substrate, p-NPP, was added to the wells, and the color that developed was quantified using an ELISA reader. All buffers and solutions used were substantially as described regarding Competitive ELISA in the "Materials and Methods" section above.

Another sample of antibody was preincubated overnight with the specific peptide, in order to analyze competition. Controls were performed as indicated in FIG. 4A, using a control peptide coating the plate instead of anti-H2a, using a control antibody instead of the specific monoclonal antibody, or preincubating the anti-H2a antibody with a control peptide.

In a similar experiment, competition was performed with several dilutions of normal human serum as indicated above. The bars represent an average of the quantification of duplicate samples.

Experimental Results

The hybridoma cell (B9) that was developed produced a monoclonal antibody that allowed for a very specific and sensitive assay, as seen in FIGS. 4a-b. In FIG. 4a different controls for the efficacy of the antibody binding are shown. The right most column represents one type of negative control, in which a control peptide is bound to the ELISA plate instead of the specific peptide. It is clearly seen that the reaction level is substantially zero. The second column from the right presents another type of negative control, in which a control antibody is present instead of the specific antibody. Also in this case it is clear that the reaction is in a very low level if at all existent. The middle column represents a positive control, in which there is a control form of competition, as the antibody is not preincubated with the specific peptide but rather with a control peptide. It is clear from the figure that the reaction level is very close to the maximal binding level. The second column from the left represents a normal testing situation, in which the antibody is preincubated (competed) with the specific peptide, and then incubated with the specific antibody on the ELISA plate. It is shown that there is an 81% inhibition of the reaction by such competition. The leftmost column represents a second negative control, in which there is no type of competition peptide at all, and according to which the 100% reaction was standardized.

FIG. 4b represents rise in inhibition of the antibodies binding to the peptide on the plate as the dilution of serum with which the antibodies are preincubated decreases. As is clearly visible from the figure, when there is no preincubation with serum (serum concentration 0) the reaction between the antibody and the peptide bound to the ELISA plate is 100% complete, and as the dilution decreases the competition is greater and therefore there is more inhibition of the antibody binding to the peptides bound to the ELISA plate.

In order to be able to measure the absolute concentration of sH2a in the sera, a recombinant version of sH2a with a 6×His-tag in its carboxy-terminus was produced. The construct is expressed in *E. coli*, and purified on a $Ni^{2+}$-NTA-sepharose column. After elution and confirmation of the purity of the recombinant protein in SDS-PAGE it can be used as a standard in the competitive ELISA assay.

Example 5

Quantitation of Serum Levels of sH2a in Patients with Liver Disease

Experimental Methods

Figure 5B:
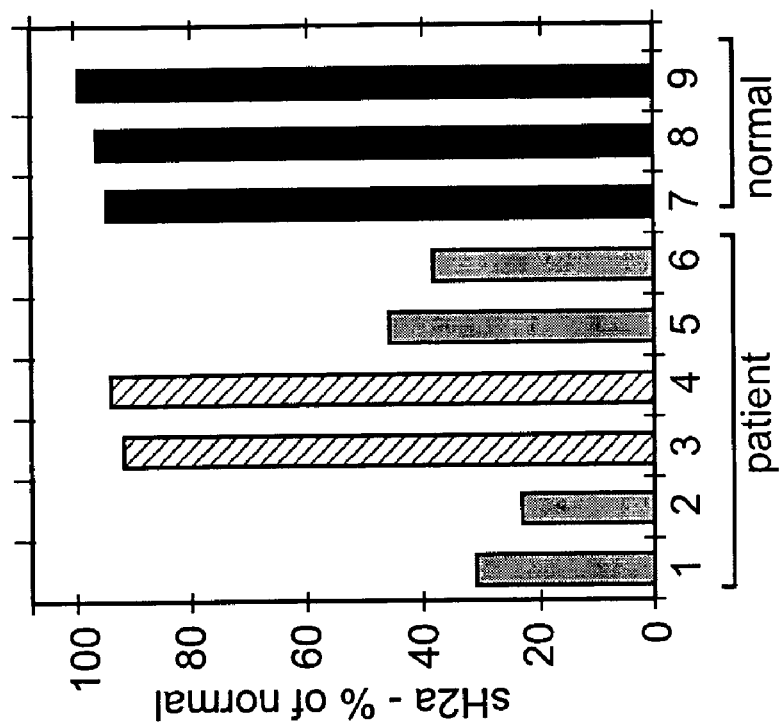
FIG. 5b demonstrates a comparison between sH2a levels in normal human sera (lanes 7-9) and in serum taken from patients with liver cirrhosis or fibrosis (lanes 1-6), as well as in samples taken from patients recovering from these diseases (lanes 3-4)
Figure 5A:
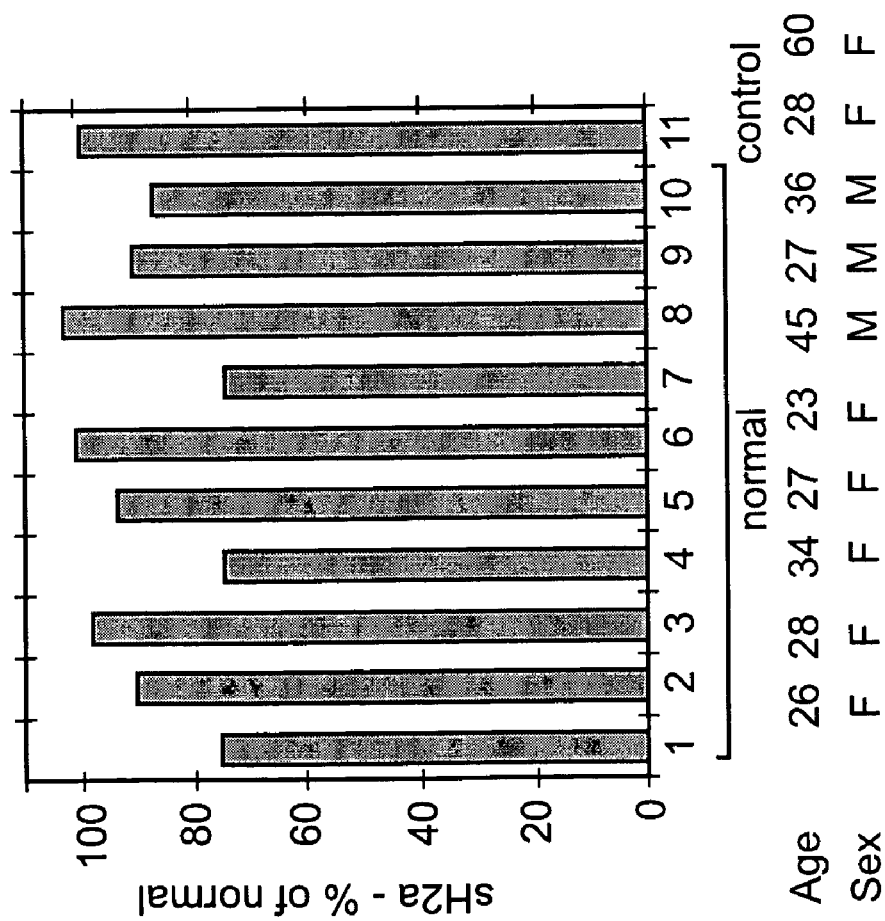
FIG. 5a demonstrates the variation in sH2a serum levels in different samples of normal human serum, obtained from males (M) and females (F) in a wide range of ages.

In a first experiment, 0.1 ml of normal human sera was analyzed using the assay described above in Example 4. Sera from female (F) and male (M) individuals of different ages as indicated in FIG. 5a were compared to a control normal sample (11). In a second experiment, serum samples from patients with cirrhosis (FIG. 5b bars 1,2), moderate fibrosis (FIG. 5b bars 5,6) or after phlebotomy treatment for moderate fibrosis (FIG. 5b bars 3,4) were analyzed for sH2a levels compared to 3 normal subjects (FIG. 5b bars 7-9) using the ELISA assay described above in Example 4.

In a third experiment, serum samples from patients with cirrhosis (FIG. 5c bars 1-4) were analyzed for sH2a levels compared to 3 normal subjects (FIG. 5c bars 5-7) using the ELISA assay described above in Example 4.

Experimental Results

Using the ELISA assay described above, many samples of normal human sera from male and female individuals in a wide range of ages were analyzed. As seen in FIG. 5a, the detected sH2a levels were substantially constant, differing by no more than 10% from the average.

At the next stage, samples from patients with liver fibrosis or cirrhosis were examined, and the results were compared to those obtained for normal human sera. There was a striking drop in the sH2a level in sera from patients with liver fibrosis. One such assay is presented in FIG. 5b. As shown, sera from six patients with fibrosis that resulted from chronic infection with Hepatitis C, was compared to three normal samples. The results clearly show that after treatment and recovery the levels of sH2a returned to normal (FIG. 5b, samples 3 and 4).

Figure 5C:
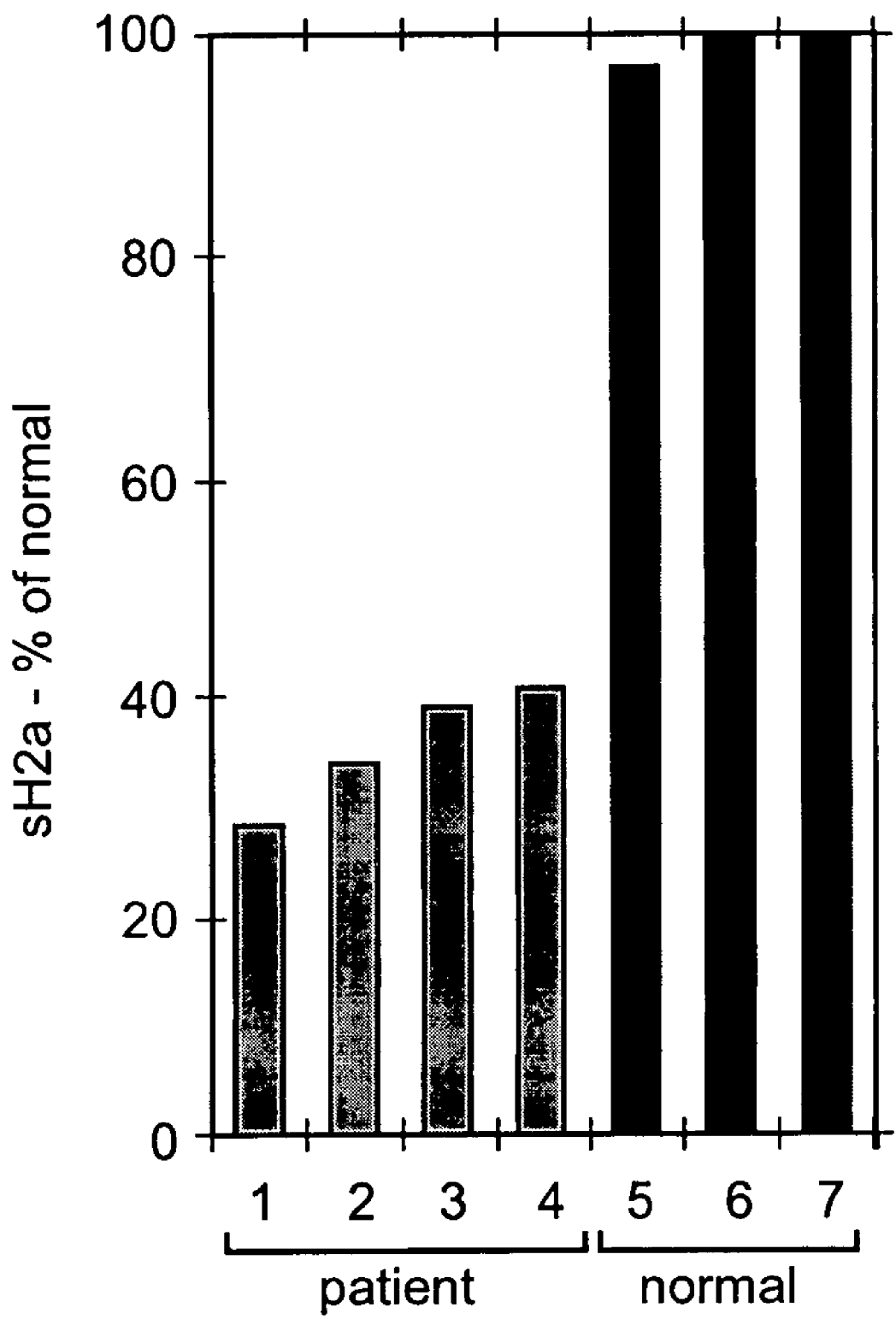
FIG. 5c demonstrates a comparison between sH2a levels in serum taken from patients with cirrhosis (lanes 1-4) and in serum from 3 normal subjects (lanes 5-7)

FIG. 5c demonstrates the comparison of sH2a levels in 4 serum samples taken from cirrhosis patients and in 3 normal serum samples. It is clear from the results that sH2a levels in cirrhosis patients is significantly lower than the level found in normal serum, and the ELISA assay described above indeed detects the difference accurately.

Serum samples of all the tested patients are obtained periodically in order to analyze the correlation of the sH2a level with the development of the disease. Histological analysis of biopsies from these patients is performed in order to determine the stage of the disease. Patient serum samples are also analyzed retrospectively, from a serum bank. Differences in the amount of the soluble H2a between normal human serum and serum from patients at different stages of the diseases can be of large importance for diagnosis. The levels of sH2a in patients before and after liver transplantation is also analyzed, and used as a measure of recovery. A successful transplant should lead to recovery of sH2a in serum to normal levels (results not shown).

Without wishing to be limited to a single hypothesis, the results suggest that the analysis of serum levels of sH2a using the developed ELISA assay constitutes a powerful diagnosis tool for the non-invasive assessment of liver fibrosis and hepatocarcinoma, as well as a measure of recovery from liver transplant. This diagnostic method could replace the invasive technique used today, liver biopsy. As explained above, none of the existing non-invasive markers are satisfactory and therefore they cannot replace liver biopsy as the diagnostic gold standard.

Example 6

Assay, Kit and Method of Use Thereof

This Example provides a number of non-limiting, illustrative embodiments of the present invention with regard to assays, kits and methods of use thereof.

A method for detection and/or staging of a liver disease comprises, for example, such processes as immobilizing an antigen that binds to at least one antibody or fragment thereof of the present invention on a support, applying the antibody, washing, adding a labeled secondary antibody, washing and detecting and/or measuring the label either directly or indirectly, which reflects the quantity of the soluble marker protein which was bound to the antibody.

Examples of the support include but are not limited to latex particles, cellulosic materials such as cellulose sheets for example, plastic assay plates and particles and the like.

The antigen used may optionally be immobilized on the support through covalent bonding or physical adsorption, for example. Examples of the sample include human sera and the like. Optionally and preferably, the surface of the support is "blocked" by pre-incubation with bovine serum albumin (BSA) or the like before the addition of a sample to at least reduce the likelihood of other antibodies in the sample binding to the support non-specifically. The support is then preferably washed with a suitable buffer, such as a surfactant-containing phosphate buffer for example, or the like.

A non-limiting example of the labeled secondary antibody is a labeled anti-mouse monoclonal antibody. Useful labels include but are not limited to various kinds of enzymes such as alkaline phosphatase, luciferase, peroxidase, beta-galactosidase and the like, and various fluorescent compounds such as fluorescein and the like. A chemical compound such as biotin, avidin, streptavidin, digoxigenin or the like may be inserted between the antibody and the label.

When the label is an enzyme, its presence may optionally be detected and/or measured by adding a substrate and detecting and/or measuring the light emission or color development which occurs due to the catalytic action of the enzyme and/or by measuring the change in light absorbance. When the label is a fluorescent compound, it may optionally be detected and/or measured by irradiating the reaction system with UV light and detecting and/or measuring the emitted fluorescence. A sensitizer may be used if necessary.

Reagents for detection and/or measurement of the marker protein sH2a using the antibodies of the present invention binding to at least one epitope of the marker preferably include the antibodies or fragments thereof, the necessary amounts of the secondary antibody and the substrate (if required), and also optionally one or more "support" reagents which are required for the action of the previously described reagents. These reagents are optionally and preferably provided in a kit. The aforementioned reagents can be used as agents for diagnosis of liver disease, for staging of liver disease, or for assessment of success of liver transplantation.

For example, a kit preferably features the monoclonal antibodies or fragments thereof. Optionally and more preferably, the kit also features a reporter component for enabling the presence of the soluble marker protein in the sample from the subject to be detected. The reporter component is preferably a suitable secondary antibody, optionally and preferably also including a label (if required) for detection of the secondary antibody. The kit may also optionally and preferably feature one or more buffers, such as a "blocking" buffer for pre-incubation with the substrate in order to block non-specific reactions with the substrate and/or proteins immobilized thereon; and one or more buffers for the sample, the secondary antibody, the substrate and/or for washing the substrate between incubations with the previously described reagents. Of course, other reagent(s) could also optionally be included as appropriate.

Optionally, the kit may provide for a competitive assay, in which a control protein will be bound to the solid phase. In this case, the antibody or fragment thereof of the present invention is preincubated with the sera sample, and then applied to the plate. The binding of the antibodies to the plate is detected by the reporter component, according to which one of ordinary skill in the art can define whether or not, and preferably the quantity of the antibody which was bound to epitopes from the sera, and thus the quantity of the soluble marker protein in the sample.

The type of reagents and/or kit, and/or the requirement for other types of equipment in addition to and/or in combination with the kit, each depend upon the type of assay being performed with the kit. Non-limiting examples of such assays, as previously described, include ELISA, Western blots or flow cytometry. The ELISA test may be competitive. An exemplary method for performing an ELISA assay was described above. Western blots are frequently more accurate than ELISA but may require more time and/or equipment to perform.

Example 7

Illustrative Kit and Method of Use Thereof

This Example describes the performance of a non-limiting illustrative kit and protocol according to the present invention. This kit was developed for a competitive ELISA assay as described in greater detail above.

The kit included at least one antibody, which was a polyclonal or a monoclonal antibody. Preferably the kit included a plurality of monoclonal antibodies or fragments thereof according to the present invention. For this non-limiting Example, the kit featured anti-sH2a carboxiterminal monoclonal antibody of hybridoma clone B9 described above. In addition, the kit preferably included at least one of the peptides used to produce the monoclonal antibodies, coated onto a multi-well plastic plate, such as a 96-well plate for example. The kit preferably also included a suitable secondary antibody, more preferably labeled with an enzyme for detecting the suitable secondary antibody. In this non-limiting Example, the enzyme was horse-radish peroxidase and a suitable substrate for the enzyme was also featured in the kit. Optionally and preferably, the kit also featured wash and/or blocking buffers as follows:

Peptide immobilization buffer: 5 µg/ml peptide in TBS (154 mM NaCl in 10 mM Tris-HCl, pH 7.5).

Blocking buffer: 3% BSA (Sigma, A4503) in TBS.

Preincubation buffer: Dilutions of serum sample were preincubated with 1:1000 dilution of primary antibody in 0.3% BSA in TBS.

Wash buffer for ELISA plate wells: TBS.

Secondary antibody: 0.08 µg/ml of goat anti-mouse IgG conjugated to Alkaline Phosphatase (Jackson, 115-055-146) in 0.3% BSA in TBS.

Enzyme (alkaline phosphatase) substrate: p-NPP, 100 µl per well, cat. No. ES009-500 mL Chemicon International (Temecula, Calif.).

The method of the kit was performed as follows in order to test the efficacy, accuracy and sensitivity of the kit according to the present invention.

Reagents were allowed to reach room temperature (20° C.-24° C.) before use.

1. 5 µg/ml of a carboxy-terminal peptide from H2a that had been used to produce the primary monoclonal antibody in mice according to the present invention was incubated in TBS for 2 hours to immobilize it on an ELISA plate.

2. The plate was blocked with 3% BSA (Sigma, A4503) in TBS for 1 hour at room temperature.

3. Eight double dilutions of human serum sample were preincubated with 1:1000 dilution of ascitic fluid containing primary monoclonal antibody according to the present invention in 0.3% BSA in TBS for 16 hours at 4° C.

4. Samples of primary monoclonal antibody that had been preincubated with dilutions of human serum sample were applied onto the plate in triplicates.

5. The plate was incubated at room temperature for 1 hour.

6. Each well was washed 3 times by filling each well with TBS, then inverting the plate vigorously to remove all water, and blotting the rim of wells on absorbent paper for a few seconds; an automated microtiter washer could also be used.

7. The plate was incubated with 0.08 µg/ml of goat anti-mouse IgG secondary antibodies conjugated to alkaline phosphatase (Jackson, 115-055-146) in 0.3% BSA in TBS, for 1 hour at room temperature.

8. Each well was washed 3 times by filling each well with TBS, then inverting the plate vigorously and blotting the rim of wells on absorbent paper as previously described.

9. Alkaline phosphatase substrate solution (p-NPP (Chemicon)) was added to the plate at 100 µl per well and incubated at 37° C. till the appearance of the color (approximately 15 minutes).

10. The developed color was quantified in an ELISA reading spectrophotometer at 620 nm wavelength.

Calculation of Results

An average of the OD values obtained for triplicates for each serum dilution is divided by the average of triplicates of values obtained for wells where antibody was added without preincubation with sera (control) and multiplied by 100. This will give percent competition for each dilution of the sample. The same calculation is done for dilutions of normal serum.

The percent of normal for each dilution of the sample is then calculated by dividing its percent competition by the percent competition by the corresponding dilution of normal serum. The final percent of normal is calculated by averaging the percents of normal obtained for each dilution of the sample.

The negative control O.D. average of four wells should not be higher than 0.06. The threshold for a positive result is O.D of at least twice the negative control average O.D value.

Example 8

Western Blot Assay for the detection of sH2a

This Example describes a non-limiting example of the polyclonal or preferably the monoclonal antibody of the present invention for use in a Western blot assay.

For this assay, proteins from the obtained sample immunoprecipitated with an anti-H2a carboxyterminal antibody, are separated in SDS polyacrylamide gel electrophoresis and transferred to a nitrocellulose filter. For this purpose, 0.3 ml of serum sample are immunoprecipitated for 16 hours at 4° C. with 20 µl of protein A-sepharose (Repligen, Cambridge, Mass.) that were crosslinked to polyclonal anti-H2a carboxyterminal antibodies with dimethyl pimelimidate (Pierce). Immunoprecipitates are washed three times with PBS and then boiled in 10 µl of 0.5% SDS in 50 mM sodium citrate pH 6.0. Then, 10 µl of a solution containing 200 mM sodium phosphate pH 8.0, 40 mM EDTA pH 8.0, 3% N-octyl-glucoside is added, together with 40 mU of N-glycosidase F (Boehringer), and incubations are carried out for 16 hours at 37° C. Twenty µl of 2× sample buffer (125 mM Tris-HCl pH 6.8, 4% SDS, 20% Glycerol, 7% β-Mercaptoethanol and Bromphenol blue) are added and the samples boiled before loading for SDS-PAGE. SDS polyacrylamide gels are prepared as follows:

10-15% Acrylamide, 2.66% Bis-Acrylamide (BDH), 375 mM Tris-HCl pH 8.8, 0.1% SDS, 0.3% ammonium peroxydisulfate (APS) (Merck) and 0.05% N,N',N'-tetramethylethylenediamine (TEMED) (BioRad). APS and TEMED are used in this context as free radical starters for the polymerization. 2-4 hours after polymerization, the stacking gel (4.5% Acrylamide, 0.12% Bis-Acrylamide, 125 mM Tris-HCl pH 6.8, 0.1% SDS, 0.1% APS, 0.1% TEMED) is poured above the resolving gel. The anode and cathode chambers are filled with identical buffer solution: 25 mM Tris base, 192 mM glycine and 0.1% SDS, pH 8.5. The antigen-containing material is treated with the same volume of sample loading buffer 125 mM Tris-HCl pH 6.8, 4% SDS, 20% Glycerol, 7% β-Mercaptoethanol, Bromphenol blue). The mixture is then heated at 100° C. for 5 minutes and loaded onto the stacking gel.

The electrophoresis is performed at room temperature for a suitable time period, for example overnight using a constant current strength of 6 mA for gels of 16 cm in size. The antigens are then transferred to nitrocellulose (Schleicher and Schuell, Dassel).

Protein transfer is performed substantially as described above. The gel is located, together with the adjacent nitrocellulose, between Whatmann 3 MM filter paper, conductive, 1 cm-thick foamed material and two carbon plates which conduct the current by way of platinum electrodes. The filter paper, the foamed material and the nitrocellulose are soaked thoroughly with blotting buffer (192 mM glycine, 25 mM tris base, 20% methanol, pH 8.5). The transfer is performed at 2 mA/cm² for 2 hours. Free binding sites on the nitrocellulose are saturated, at room temperature for 1 hour, with 5% milk in TBS. The blot strips are incubated with an antibody or fragment thereof according to the present invention (dilution, 1:500 in 0.5% milk in TBS (154 mM NaCl and 10 mM Tris-HCl, pH 7.5)) at 4° C. overnight.

After incubation with the antibody or fragment thereof, the blot is washed four times for in each case 5 minutes with TTBS (50 mM Tris-HCl, pH 7.5, 500 mM NaCl, 0.01% Tween 20). The blot strips are then incubated, at room temperature for 1 hour, with peroxidase-coupled suitable IgG immunoglobulin (Jackson 115035-146, dilution 1:2500 in 0.5% milk in TBS. After having been washed several times with TBS, the blot strips are incubated with ECL solutions (2.5 mM Luminol, 400 µM Para Coumaric acid, 5.4 mM $H_2O_2$ in 100 mM Tris-HCl pH 8.5), prepared fresh just before use, and exposed to Fuji film 100 NIF.

If sH2a is present in the sample from the subject, a detectable signal should appear at the appropriate location for the antigen.

Example 9

The Use of sH2a as a Sensitive Marker for Liver Function

Experimental Methods

Competitive ELISA—Corning ELISA plate wells were coated with the carboxyterminal peptide of H2a (5 µg/ml) and blocked with 3% BSA. Ascitic fluid containing anti-peptide monoclonal antibody (1:1000) (described under Materials and Experimental Methods hereinabove) was preincubated with 8 double dilutions of the serum sample overnight at 4° C. It was then added to the coated ELISA plate wells and incubated for 1 hour at RT. The wells were washed with TBS and reacted for 1 hour at RT with goat anti-mouse IgG conjugated to alkaline phosphatase (Jackson, 1:2500). After adding an alkaline phosphatase substrate [p-NPP, 100 µl per well, cat. No. ES009-500 mL Chemicon International, (Temecula, Calif.)] the OD was quantified using an ELISA reader at a wavelength of 410 nm.

ALT, albumin, PT, bilirubin and ALP tests—Standard routine tests were used in all cases.

Experimental Results

Quantitation of the serum levels of sH2a in HCV patients with or without liver fibrosis—Samples of sera from HCV patients with or without liver fibrosis were analyzed by an ELISA assay, essentially as described under Materials and Experimental Methods hereinabove. The patient's sera was compared to normal human sera at various time-points to reveal ALT and sH2a level during therapy for about a year. FIGS. 6a-b show comparative analyses of the percent of sH2a in serum compared to normal and the normalized ALT level in serum of a patient (patient No. 1) with mild liver fibrosis. The first sample was taken prior to treatment and then the patient was treated with interpheron alpha and ribavirin. Thus, prior to treatment, the ALT level of patient No. 1 was abnormal and, upon treatment, was reduced to the normal range (i.e., less than 1) (FIG. 6a). On the other hand, sH2a levels displayed an almost mirror image, starting with low abnormal levels (i.e., less than 85% of normal) and, upon treatment, increasing to normal levels (FIG. 6b). Interestingly, there was a delay of about 10 weeks between the time point in which ALT levels reached normal levels to the time point in which sH2a levels were back to normal. This is probably due to the fact that ALT levels reflect on liver damage while sH2a levels reflect on liver function (sH2a). Thus, in order to recover to a normal function following liver damage (as reflected by ALT levels) an additional time is required (as reflected by sH2a levels).

Figure 7A:
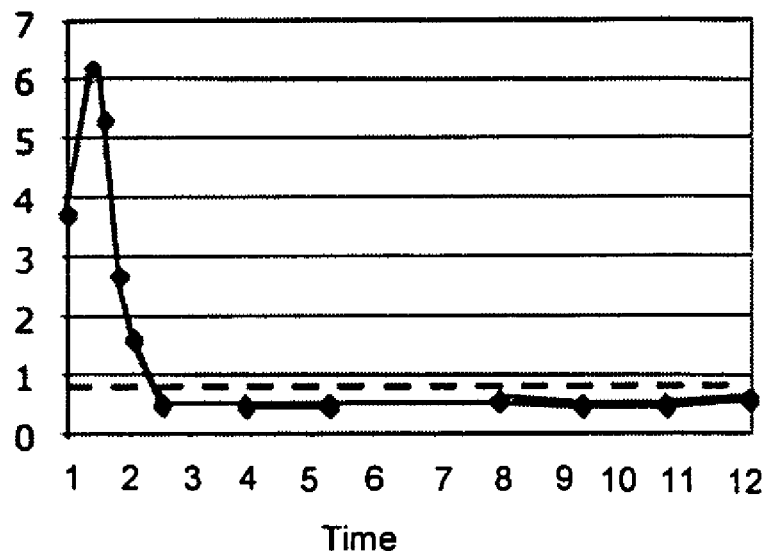
FIGS. 7a-b are graphs depicting ALT (FIG. 7a) and sH2a (FIG. 7b) levels in patient 2 with moderate liver fibrosis along a period of 11 months. Samples of serum were taken before treatment with ribavirin and alpha-interpheron (first data point, No. 1) and at pre-determined times (in one month intervals) after treatment; No. 2=1 month post-treatment, No. 3=2 months post-treatment, No. 4=3 months post-treatment, No. 5=4 months post-treatment, No. 6=5 months post-treatment, No. 7=6 months post-treatment, No. 8=7 months post-treatment, No. 9=8 months post-treatment, No. 10=9 months post-treatment, No. 11=10 months post-treatment, No. 12=11 months post-treatment. Treatment and measurements of ALT and sH2a levels were performed as described in FIGS. 6a-b.
Figure 7B:
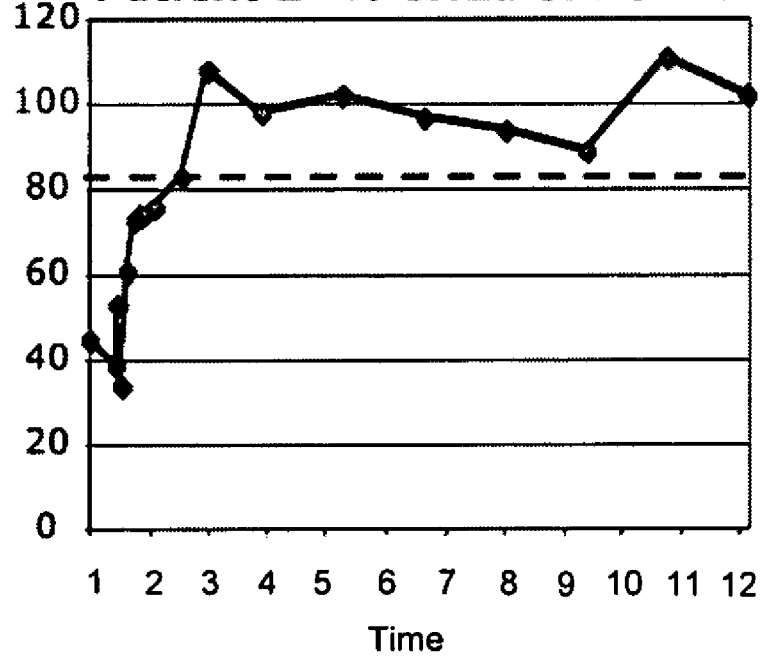
Figure 8A:
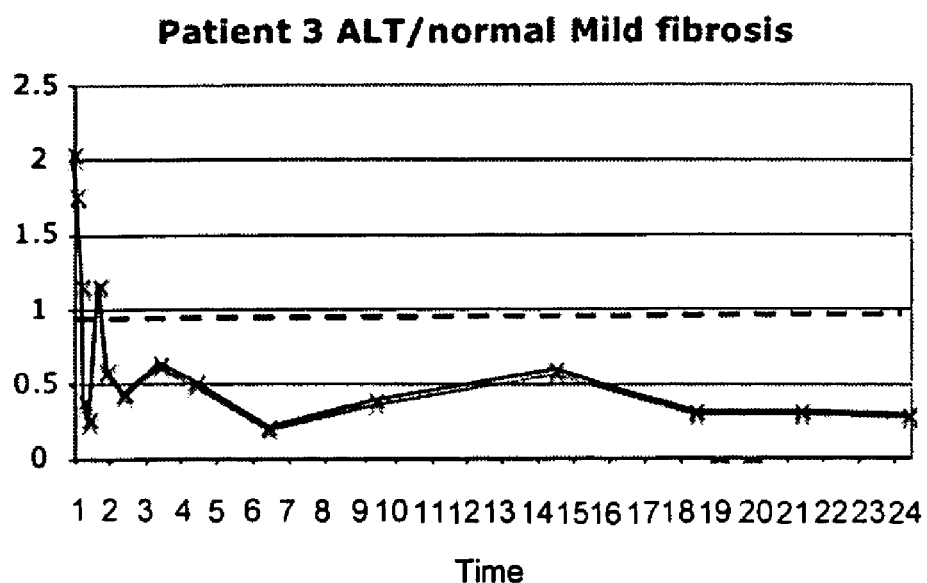
FIGS. 8a-b are graphs depicting ALT (FIG. 8a) and sH2a (FIG. 8b) levels in patient 3 with mild liver fibrosis along a period of 11 months. Samples of serum were taken before treatment with ribavirin and alpha-interpheron (first data point, No. 1) and at pre-determined times (in two-weeks intervals) after treatment; No. 2=2-weeks post-treatment, No. 3=4-weeks post-treatment, No. 4=6-weeks post-treatment, No. 5=8-weeks post-treatment, No. 6=10-weeks post-treatment, No. 7=12-weeks post-treatment, No. 8=14-weeks post-treatment, No. 9=16-weeks post-treatment, No. 10=18-weeks post-treatment, No. 11=20-weeks post-treatment, No. 12=22-weeks post-treatment, No. 13=24-weeks post-treatment, No. 14=26-weeks post-treatment, No. 15=28-weeks post-treatment, No. 16=30-weeks post-treatment, No. 18=32-weeks post-treatment, No. 19=34-weeks post-treatment, No. 20=36-weeks post-treatment, No. 21=38-weeks post-treatment, No. 22=40-weeks post-treatment, No. 23=42-weeks post-treatment, No. 24=44-weeks post-treatment. Treatment and measurements of ALT and sH2a levels were performed as described in FIGS. 6a-b.
Figure 8B:
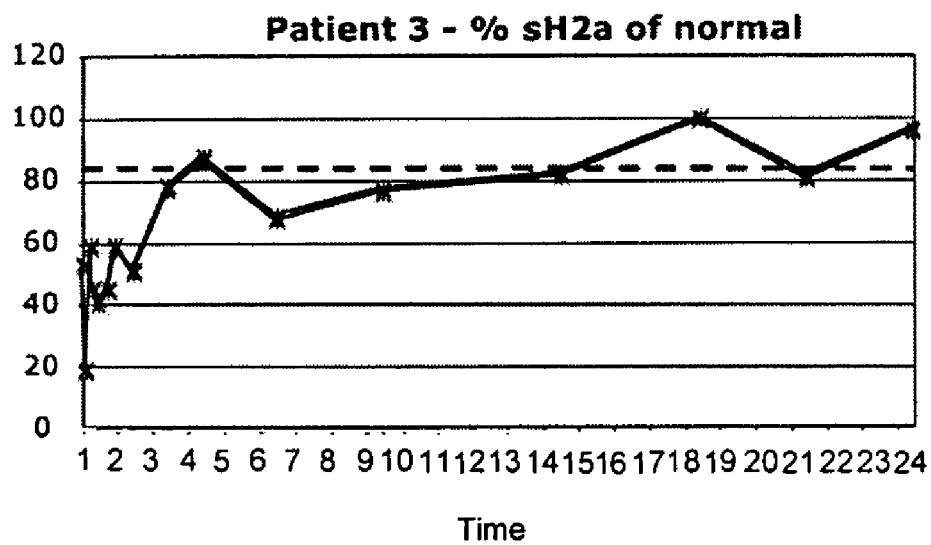
Figure 9A:
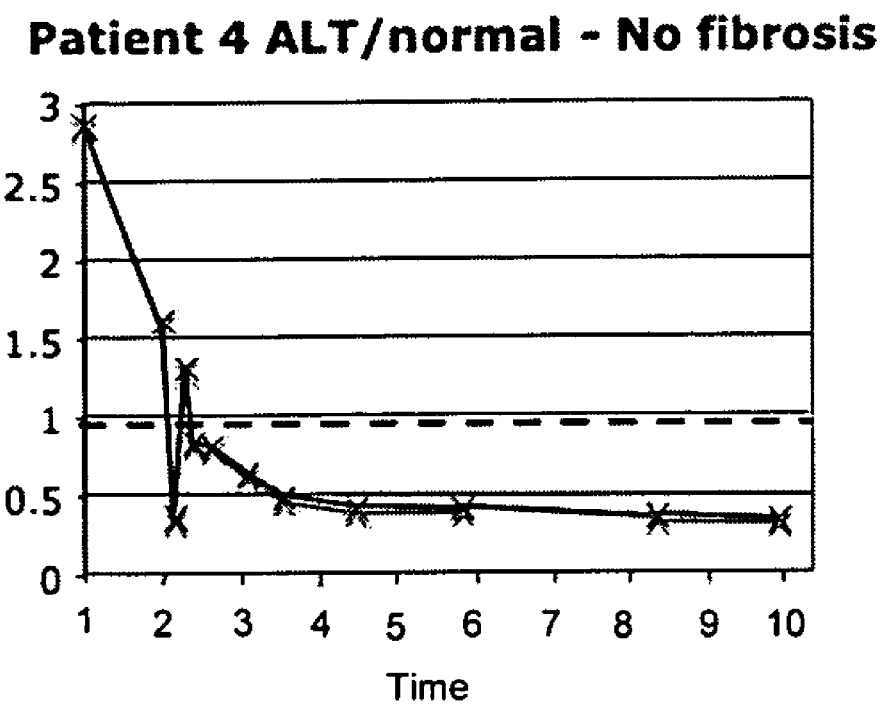
FIGS. 9a-b are graphs depicting ALT (FIG. 9a) and sH2a (FIG. 9b) levels in Patient 4 with no liver fibrosis but with liver inflammation along a period of 9 months. Samples of serum were taken before treatment with ribavirin and alpha-interpheron (first data point, No. 1) and at pre-determined times (in one month intervals) after treatment; No. 2=1 month post-treatment, No. 3=2 months post-treatment, No. 4=3 months post-treatment, No. 5=4 months post-treatment, No. 6=5 months post-treatment, No. 7=6 months post-treatment, No. 8=7 months post-treatment, No. 9=8 months post-treatment, No. 10=9 months post-treatment, No. 11=10 months post-treatment. The treatment and the measurements of ALT and sH2a levels were performed as described in FIGS. 6a-b.
Figure 9B:
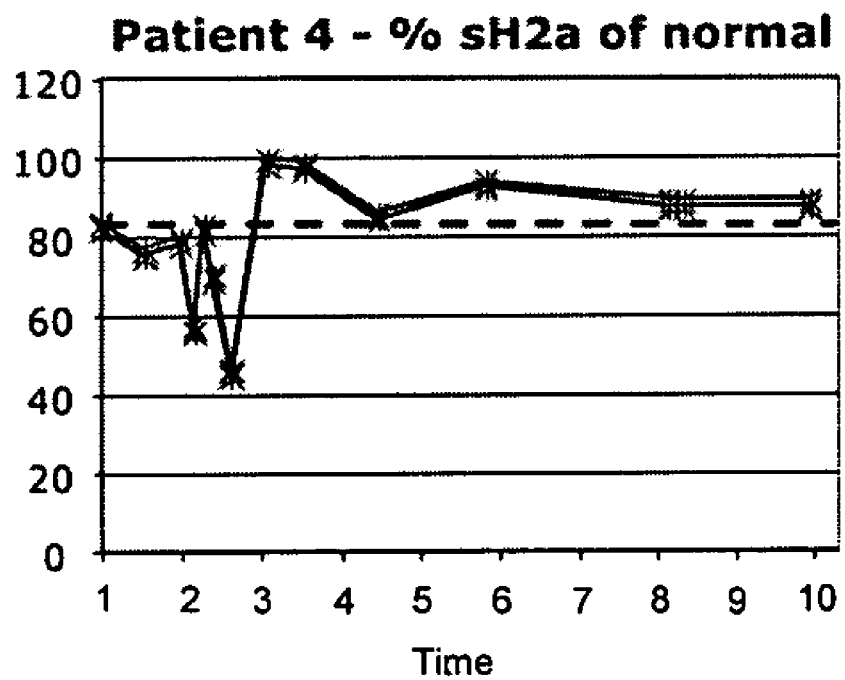

Similarly, in the serum derived from patients Nos. 2, with moderate liver fibrosis (FIGS. 7a-b) and 3, with mild liver fibrosis (FIGS. 8a-b) there was a delay between the time point in which ALT returned to normal levels and that when sH2a showed normal values, but the delay was shorter than that for Patient No. 1. FIGS. 9a-b demonstrate the results for patient No. 4 with no fibrosis, but with inflammation of the liver, who showed initial high levels of ALT, whereas his level of sH2a was normal, although borderline.

Analysis

High ALT levels would suggest damage of liver cells, but there could still be normal function of most of the mass of liver cells that are still not damaged, which can be reflected by relatively normal levels of sH2a. After the beginning of treatment there was a temporary reduction in the levels of sH2a as the therapy itself may have an initial effect on liver function. The levels of sH2a then recovered to normal (FIG. 9b). For all 4 patients the classical liver function tests of albumin level and prothrombin time showed results in the normal range, although the patients showed clear external signals of compromise in their liver function. As stated above, albumin and PT tests show abnormal levels only in very severe cases. Bilirubin and alkaline phosphatase levels were also in the normal range for these patients with mild disease.

The studies presented herein indicate a striking drop in serum levels of sH2a in liver fibrosis and cirrhosis patients. The levels of sH2a recovered very rapidly in patients that responded to therapy. The patients that were studied had mild fibrosis (at a stage that still responds to therapy) and therefore showed normal levels for ALP, albumin and prothrombin time, markers that can only detect severe disease. Levels of sH2a were normal in HCV patients with liver inflammation but no fibrosis, in contrast to their elevated levels of ALT.

These results suggest that the analysis of serum levels of sH2a using the ELISA assay according to the method of the present invention could constitute a powerful diagnosis tool for the determination of liver function. This would be the first described true specific and sensitive test for liver function. It would be able to assess liver function status in standard tests and diagnose the recovery of liver function in diverse liver diseases or after liver transplant. This diagnostic method can even replace the invasive technique used today as the gold standard for accurate assessment of liver function and disease, liver biopsy.

Altogether, these results demonstrate that the level of the soluble form of the human asialoglycoprotein receptor (AS-GPR), sH2a, in the blood is a sensitive marker for liver function for which the existing markers are not satisfactory. ASGPR sH2a is expressed exclusively in hepatocytes and was found to exhibit constant levels in normal human serum. While the current markers of liver function reveal only cases of severe liver disease (PT, albumin) and are affected in some non-hepatic diseases, the other markers currently used (e.g., ALT, AST, GGT, ALP, etc.) are indicative of liver damage, which is not directly related to the liver function. In addition, these enzymes are not specific to the liver and their levels are increased in many non-hepatic diseases. Altogether the results suggest that sH2a is a sensitive marker for liver function, superior to known markers. The detection method involves an ELISA assay that was developed by the present invention for the analysis of the levels of sH2a in serum from patients and comparison with healthy subjects.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Additional References are Cited in Text

1. Trojan, J., J. Raedle, and S. Zeuzem, Serum tests for diagnosis and follow-up of hepatocellular carcinoma after treatment. Digestion, 1998. 59 Suppl 2: p. 72-4.
2. Hayasaka, A. and H. Saisho, Serum markers as tools to monitor liver fibrosis. Digestion, 1998.59(4): p. 381-4.
3. Drickamer, K., Clearing up glycoprotein hormones. Cell, 1991. 67(6): p. 1029-1032.
4. Doyle, D. B., Y and Petell, J, ed. The Liver: Biology and Pathobiology., ed. I. J. Arias, W B; Popper, H; Schachter, D and Shafritz, D A. 1988, Raven Press. 141.
5. Lederkremer, G. Z. and H. F. Lodish, An alternatively spliced miniexon alters the subcellular fate of the human asialoglycoprotein receptor H2 subunit. Endoplasmic reticulum retention and degradation or cell surface expression. J Biol Chem, 1991. 266(2): p. 1237-44.
6. Tolchinsky, S., M. H. Yuk, M. Ayalon, H. F. Lodish, and G. Z. Lederkremer, Membrane-bound versus secreted forms of human asialoglycoprotein receptor subunits—Role of a juxtamembrane pentapeptide. J Biol Chem, 1996. 271(24): p. 14496-14503.
7. Yago, H., Y. Kohgo, J. Kato, N. Watanabe, S. Sakamaki, and Y. Niitsu, Detection and quantification of soluble asialoglycoprotein receptor in human serum. Hepatology, 1995. 21(2): p. 383-388.
8. Gopal, D. V., and Rosen, H. R. (2000) Abnormal findings on liver function tests. Interpreting results to narrow the diagnosis and establish a prognosis. Postgrad Med 107, 100-102, 105-109, 113-104.
9. Hay, J. E., et al. (1989) The nature of unexplained chronic aminotransferase elevations of a mild to moderate degree in asymptomatic patients. Hepatology 9, 193-197.
10. Moseley, R. H. (1996) Evaluation of abnormal liver function tests. Med Clin North Am 80, 887-906.

What is claimed is:

1. A method of testing liver function in a subject, the method comprising:
   (a) detecting a level of sH2a in a biological sample of the subject; and
   (b) comparing said level of sH2a with a level of sH2a in samples from normal subjects,
   wherein detecting a level of said sH2a in said sample above or below a level of sH2a in normal subjects is indicative of abnormal liver function, and wherein said sH2a comprises an amino acid sequence as set forth in SEQ ID NO:2.

2. The method of claim 1, wherein said sample is selected from the group consisting of a serum sample, a plasma sample, a urine sample, a whole blood sample and a blood fraction sample.

3. The method of claim 1, performed with a monoclonal antibody or fragment thereof capable of specifically binding to at least one epitope of sH2a.

4. The method of claim 3, wherein said at least one epitope is as set forth in SEQ ID NO:1.

5. The method of claim 1, performed with a polyclonal antibody.

6. The method of claim 5, wherein said polyclonal antibody specifically binds SEQ ID NO:1 or 2.

7. A method of testing liver function in a subject at risk for liver disease, the method comprising:
   (a) obtaining a biological sample from a subject at risk for liver disease;
   (b) detecting a level of sH2a in said biological sample of said subject; and
   (c) comparing said level of sH2a with a level of sH2a in samples from normal subjects,
   wherein detecting a level of said sH2a in said sample above or below a level of sH2a in normal subjects is indicative of abnormal liver function, and wherein said sH2a comprises an ammo acid sequence as set forth in SEQ ID NO:2.

8. The method of claim 1, wherein said sH2a comprises an sH2a exoplasmic domain.

9. The method of claim 7, wherein said sH2a comprises an sH2a exoplasmic domain.

* * * * *